US009321082B2

(12) United States Patent
Ona

(10) Patent No.: US 9,321,082 B2
(45) Date of Patent: Apr. 26, 2016

(54) ULTRASONIC TRANSDUCER, MANUFACTURING METHOD THEREOF, AND ULTRASONIC PROBE

(75) Inventor: Yasuhiro Ona, Nasushiobara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 104 days.

(21) Appl. No.: 14/000,189

(22) PCT Filed: May 18, 2012

(86) PCT No.: PCT/JP2012/062866
§ 371 (c)(1),
(2), (4) Date: Aug. 16, 2013

(87) PCT Pub. No.: WO2012/157769
PCT Pub. Date: Nov. 22, 2012

(65) Prior Publication Data
US 2014/0070668 A1     Mar. 13, 2014

(30) Foreign Application Priority Data
May 18, 2011   (JP) .................................. 2011-111392

(51) Int. Cl.
*H01L 41/08* (2006.01)
*B06B 1/06* (2006.01)
*B06B 3/00* (2006.01)
*A61B 8/00* (2006.01)

(52) U.S. Cl.
CPC ............. *B06B 1/0622* (2013.01); *B06B 1/0629* (2013.01); *B06B 3/00* (2013.01); *A61B 8/4444* (2013.01); *Y10T 29/42* (2015.01)

(58) Field of Classification Search
CPC ...... B06B 1/0622; B06B 1/0629; B06B 3/00; B06B 1/0607; Y10T 29/42; Y10T 29/49005; A61B 8/4444; A61B 8/4483; A61B 8/4494; H01L 41/27

USPC ................ 310/334, 336, 335, 365, 366, 311; 600/447; 29/25.35, 594; 367/153; 381/191

See application file for complete search history.

(56) References Cited

U.S. PATENT DOCUMENTS 4,583,018 A * 4/1986 Izumi et al. .................... 310/334
6,607,491 B2 * 8/2003 Sato ............................... 310/311
(Continued)

FOREIGN PATENT DOCUMENTS

| CN | 1423125 A | 6/2003 |
| CN | 101536545 A | 9/2009 |

(Continued)

OTHER PUBLICATIONS

International Search Report with English Translation for International Application No. PCT/JP2012/062866 mailed on Jul. 17, 2012.
(Continued)

*Primary Examiner* — Thomas Dougherty
*Assistant Examiner* — Karen B Addison
(74) *Attorney, Agent, or Firm* — Yoshida & Associates, LLC

(57) ABSTRACT

The purpose is to provide an ultrasonic transducer and ultrasonic probe without the complexity of the manufacturing process of a non-conductive acoustic matching layer while ensuring the conductive path. In the non-conductive acoustic matching layer comprising the first surface of the electrode side and the second surface of the opposite side of the piezo-electrics, a plurality of first grooves leading up to the mid-way point between the first surface and the second surface are arranged on each of the first surfaces of the non-conductive acoustic matching later in response to the arrangement of sound elements. Moreover, each of the second surfaces is provided with the plurality of second grooves leading up to at least the mid-way point from the second surface, intersecting the first grooves.

17 Claims, 16 Drawing Sheets

(56) References Cited

U.S. PATENT DOCUMENTS

| | | | |
|---|---|---|---|
| 6,894,425 B1 * | 5/2005 | Solomon et al. | 310/334 |
| 7,598,658 B2 * | 10/2009 | Takeuchi et al. | 310/334 |
| 2003/0127949 A1 | 7/2003 | Nagahara et al. | |
| 2010/0066207 A1 | 3/2010 | Saito | |

FOREIGN PATENT DOCUMENTS

| | | |
|---|---|---|
| JP | 62-34500 A | 2/1987 |
| JP | 7-37107 U | 7/1995 |
| JP | 2008-244859 A | 10/2008 |
| JP | 2009-130611 A | 6/2009 |
| JP | 2009-177342 A | 8/2009 |
| KR | 10-1080676 B1 | 11/2011 |

OTHER PUBLICATIONS

Chinese Office Action with its English Summary for the corresponding Chinese Patent Application No. 201280022228.X mailed on Sep. 6, 2015.

* cited by examiner ly used as the substrate. However, mismatching occurs when the FPCs are directly connected to the electrode of the piezoelectrics. For example, if the acoustic impedance value of the FPCs is approximately 3 Mrayl, as mentioned above, nonconformity of the acoustic impedance occurs between the body tissues and the piezoelectrics. Accordingly, the FPCs must be established via several acoustic matching layers mentioned above. When arranging the non-conductive acoustic matching layer on the first layer, the non-conductive acoustic matching layer is present between the electrode of the piezoelectrics and the electrode on the FPCs, consequently electrical connection is not performed. That is, a conductive path must be provided on the non-conductive acoustic matching layer.

ULTRASONIC TRANSDUCER, MANUFACTURING METHOD THEREOF, AND ULTRASONIC PROBE

FIELD OF THE INVENTION

The embodiment of the present invention relates to an ultrasonic transducer, the manufacturing method thereof, and an ultrasonic probe.

BACKGROUND OF THE INVENTION

An ultrasonic probe comprises a plurality of piezoelectrics. Moreover, electrodes are arranged on both sides of the piezoelectronics such that they interleave the piezoelectronics. There are various ways of guiding electrodes regarding the piezoelectronics. For example, one method involves conducting electrodes arranged in front surface, which is the surface of the ultrasonic radiation direction side of the piezoelectrics, with FPC (Flexible Printed Circuits). Signals derived from FPC are transmitted to a transmitter-receiver circuit.

Generally, the acoustic impedance of body tissues is approximately 1.5 Mrayl. Moreover, the acoustic impedance of piezoelectrics is 30 Mrayl or more. In other words, there is a large difference in impedance between body tissues and piezoelectrics. Therefore, acoustic mismatching occurs when body tissues are directly contacted to piezoelectrics. As a result, ultrasonic beams are reflected at borders with greatly different acoustic impedance. Accordingly, an acoustic matching layer is necessary between body tissues and piezoelectrics. The acoustic matching layer is an intermediate layer that efficiently propagates ultrasonic waves.

Moreover, in order to reduce and alleviate the acoustic mismatching mentioned above, a plurality of acoustic matching layers is sometimes configured. In the configuration, a plurality of acoustic matching layers with different acoustic impedance between the acoustic impedance of the body tissue (for example, 1.5 Mrayl) and the acoustic impedance of piezoelectrics (for example, 30 Mrayl) is gradually layered.

In the configuration, for example, if the acoustic impedance of first layer in the acoustic matching layer is approximately 9 to 15 Mrayl, a machinable ceramic is used as a material with such acoustic impedance. Machinable ceramics are mainly composed of mica and are non-conductive material.

Here, a driving voltage must be applied to the piezoelectrics in order to transmit ultrasonic waves. The electrode provided to the piezoelectrics and the driving circuit of the ultrasonic diagnostic equipment are connected using cables, etc., in order to apply the driving voltage. Moreover, when receiving ultrasonic waves, the received signals must be extracted from the piezoelectrics. In order to extract the received signals, the electrode of the piezoelectrics and the driving circuit of the ultrasonic diagnostic equipment are connected using cables, etc. As a principle measure for electrically connecting with piezoelectrics, one method uses an electrode pattern formed on substrates with relatively small acoustic impedance. FPCs are mainly used as the substrate. However, mismatching occurs when the FPCs are directly connected to the electrode of the piezoelectrics. For example, if the acoustic impedance value of the FPCs is approximately 3 Mrayl, as mentioned above, nonconformity of the acoustic impedance occurs between the body tissues and the piezoelectrics. Accordingly, the FPCs must be established via several acoustic matching layers mentioned above. When arranging the non-conductive acoustic matching layer on the first layer, the non-conductive acoustic matching layer is present between the electrode of the piezoelectrics and the electrode on the FPCs, consequently electrical connection is not performed. That is, a conductive path must be provided on the non-conductive acoustic matching layer.

For example, in a two-dimensional array ultrasonic transducer, electrodes must be derived to the FPCs from each of a huge number of elements. Accordingly, in conventional ultrasonic transducers, a through hole is formed with respect to the non-conductive acoustic matching layer, the through hole comprising electric conductivity provided in correspondence with the number and arrangement of the piezoelectrics in the layering direction. In the ultrasonic transducer, the same number of through holes as the piezoelectrics is formed on the acoustic matching layer, and the conductive path is secured by, for example, plating the entire surface of the through holes.

Moreover, in the conventional manufacturing method of ultrasonic transducers, a conductive film is provided on both surfaces of the board of the non-conductive material, and the acoustic matching layer is formed by overlapping both surfaces of the conductive film of the board thereof. That is, the non-conductive material formed by overlapping the surfaces of the conductive film of the board comprises the conductive path toward the layering direction. As an example, a board of non-conductive material having the same width as the pitch of piezoelectrics is formed, with the conductive film provided on both surfaces thereof. The boards are overlapped in a number corresponding to the number of columns or rows of the piezoelectrics to form several blocks. Furthermore, the blocks are further overlapped to form the acoustic matching layer. In the acoustic matching layer formed by the process, the board and a superposed plane of the board function as the conductive path of the electrode and the FPC.

PRIOR ART DOCUMENTS

Patent Documents

[Patent Document 1] Japanese published unexamined application 2009-130611

[Patent Document 2] Japanese published unexamined application 2009-177342

SUMMARY OF THE INVENTION

Problem to be Solved by the Invention

However, according to the manufacturing method, the manufacturing process becomes complicated. Moreover, alignment is difficult, resulting in high manufacturing costs. For example, in the process of manufacturing the through holes in correspondence with the number and arrangement of the piezoelectrics, there is a risk of the cost being increased, and moreover, the operation involving ensuring the accuracy of the through hole position is difficult. Moreover, the manufacturing process of the acoustic matching layer involving providing the conductive film on the board configured from the non-conductive material and then overlapping this is complicated, with a danger of causing further increase in the manufacturing cost and lead time in the manufacturing process of the acoustic matching layer.

The purpose of this embodiment is to provide an ultrasonic transducer that may ensure a conductive path between the substrate and the electrode of the piezoelectrics while avoiding complications in the manufacturing process of the non-conductive acoustic matching layer, as well as the manufacturing method and ultrasonic probe thereof.

Means of Solving the Problem

The ultrasonic transducer related to this embodiment comprises a plurality of piezoelectrics, electrodes provided to each of the piezoelectrics, a non-conductive acoustic matching layer, and a substrate. The piezoelectrics are two-dimensionally arranged. Furthermore, the non-conductive acoustic matching layer comprises a first surface of the electrode side and a second surface, which is the opposite side of the first surface. The substrates are arranged on the second surface side. A plurality of first grooves leading up to the mid-way point between the first surface and the second surface are respectively arranged on the first surface of the non-conductive acoustic matching layers divided according to the sequence of sound elements. Moreover, each of the second surfaces of the non-conductive acoustic matching layer are provided with a plurality of second grooves leading up to at least the mid-way point from the second surface that intersects with the first grooves. The electrode and the second surface of the non-conductive acoustic matching layer are conducted via the first grooves, the crossing part (intersection) of the first grooves and the second grooves, and the second grooves.

MODE FOR CARRYING OUT THE INVENTION

In the following, the ultrasonic transducer and the ultrasonic probe related to the present embodiment are described with reference to FIGS. 1 to 18.
[Embodiment 1]
(Schematic Configuration of the Ultrasonic Transducer)

Figure 1:
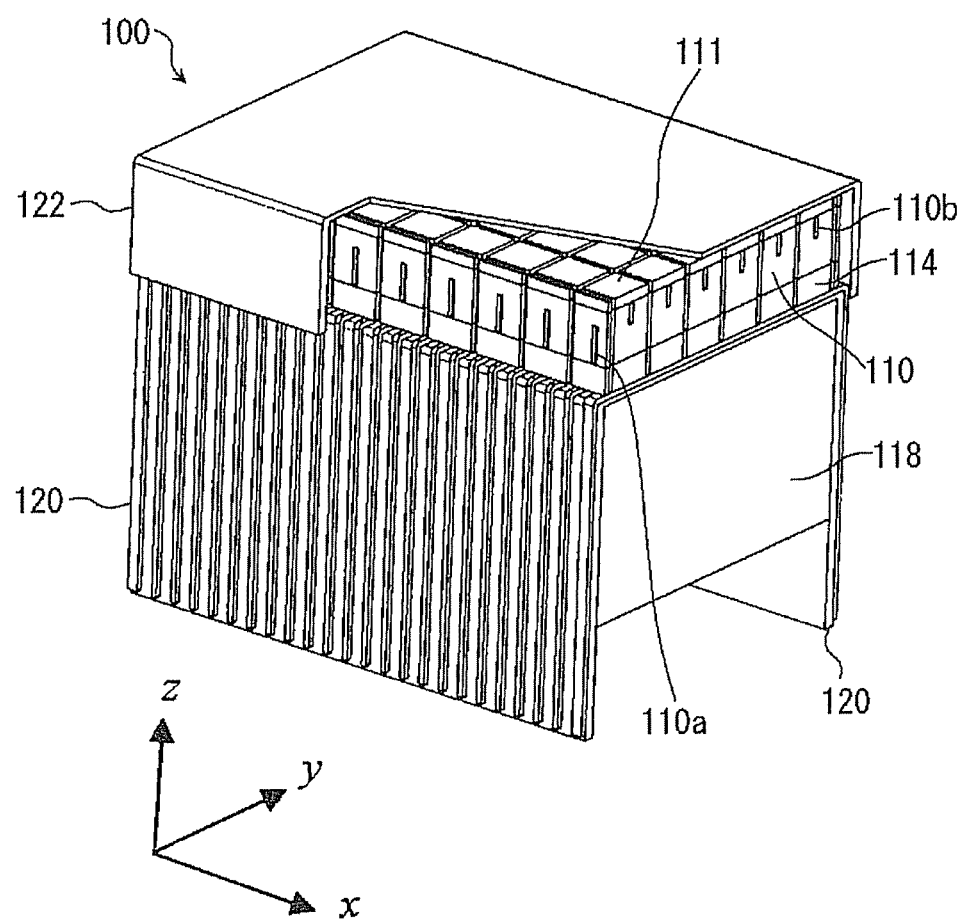
[FIG. 1] is a schematic perspective view showing the outline of the ultrasonic transducer related to Embodiment 1.

The outline of an ultrasonic transducer 100 related to Embodiment 1 is described with reference to FIGS. 1 to 3. FIG. 1 is a schematic perspective view showing the outline of the ultrasonic transducer 100. The schematic configuration of the ultrasonic transducer 100 related to the present embodiment is described in the following. Furthermore, the number of sequences of the piezoelectrics 114 of the ultrasonic transducer 100 shown in FIG. 1 is shown as a concept. Moreover, the illustrated shape of the entire arrangement, for example, the number of columns and number of rows in the two-dimensional array, is no more than one example, and other configurations may be applied.

Moreover, in the description below, the direction from a backing material 118 to a conductive acoustic matching layer 111 is referred to as the "front" (z direction in FIG. 1). The direction of the front and the opposite side is referred to as the "rear." Moreover, the front side surface of each component part in the ultrasonic transducer 100 is referred to as the "front surface." The surface of the rear side is referred to as the "back surface." Furthermore, the front surface of the non-conductive acoustic matching layer 110 corresponds to an example of "the second surface," while the back surface corresponds to an example of "the first surface."

As shown in FIG. 1, in the ultrasonic transducer 100 related to this embodiment, the piezoelectrics 114 are two-dimensionally arranged on the xy surface. Moreover, the non-conductive acoustic matching layer 110 is provided corresponding to each front surface of the respective piezoelectrics 114. Furthermore, the conductive acoustic matching layer 111 is provided on the front surface side of the non-conductive acoustic matching layer 110. Moreover, the backing material (material load phase) 118 is provided on the back surface side of the piezoelectrics 114, with a rear substrate 120 provided between the backing material 118 and the piezoelectrics 114. Moreover, in the ultrasonic transducer 100, the rear substrate 120 is derived on at least the circuit side of a subsequent stage such as a transmitter-receiver circuit; however, in FIG. 1, an illustration of the section of the rear substrate 120 is omitted.

Moreover, as shown in FIG. 1, a front substrate 122 is provided on the front surface side of the conductive acoustic matching layer 111. An acoustic lens (not illustrated) is further provided on the front surface of the front substrate 122. Moreover, in the same manner as the rear substrate 120, an illustration of the part extending to the circuit of the subsequent stage is also omitted from the front substrate 122 of FIG. 1. Moreover, a front surface electrode 112 is provided on the front surface side of the piezoelectrics 114. The front surface electrode 112 is adjacent to the back surface of the non-conductive acoustic matching layer 110. Furthermore, a back surface electrode 116 is provided on the back surface side of the piezoelectrics 114.

(Configuration of Each Part)

The configuration of each part in the ultrasonic transducer 100 related to Embodiment 1 is described in the following.

<Piezoelectric>

The piezoelectrics 114 convert the voltage applied to the back surface electrode 116 and the front surface electrode 112 into an ultrasonic pulse. The ultrasonic pulse is wave-transmitted to a subject as a test object of the ultrasonic diagnostic equipment. Moreover, the piezoelectrics 114 receive a reflected wave from the subject and convert this into voltage. As the material of the piezoelectrics 114, generally, PZT (lead zirconate titanate/Pb (Zr,Ti) $O_3$), barium titanate (BaTiO$_3$), PZNT (Pb (Zn$_{1/3}$Nb$_{2/3}$) O3-PbTiO3) single crystal, PMNT (Pb (Mg$_{1/3}$Nb$_{2/3}$) O3-PbTiO3) single crystal, etc., may be used. The acoustic impedance of the piezoelectrics 114 is, for example, approximately 30 Mrayl. Furthermore, although the piezoelectrics 114 in FIG. 1 are configured as a single layer, they may also be configured as multiple layered piezoelectrics 114.

<Backing Material>

The backing material 118 absorbs the ultrasonic pulse emitted in the irradiation direction of the ultrasonic wave and the opposite side (rear) when wave-transmitting the ultrasonic pulse, suppressing excess vibrations of the respective piezoelectrics 114. By means of the backing material 118, reflection from the back surface of the respective piezoelectrics 114 during vibration may be suppressed. In other words, by means of the backing material 118, any negative influence caused during transmission and receiving of the ultrasonic pulse may be avoided. Moreover, as the backing material 118, from the perspective of acoustic attenuation, acoustic impedance, etc., any materials such as an epoxy resin containing PZT powder, tungsten powder, etc., rubber filled with polyvinyl chloride and/or ferrite powder, or porous ceramic impregnated with resin such as epoxy, etc. may be used.

<Front Substrate, Rear Substrate>

As the front substrate 122 and the rear substrate 120, for example, a FPC (Flexible Printed Circuits) may be used. Moreover, the front substrate 122 and the rear substrate 120 are each of a length leading to the circuit of the subsequent stage of the transmitter-receiver circuit or a connection of the cable, etc. Moreover, each of the front substrate 122 and the rear substrate 120 are provided with a connecting lead (not illustrated) connected to the circuit of the subsequent stage. The connecting lead is provided on one or both of the front surface side and the back surface side of each of the front substrate 122 and the rear substrate 120. Regarding the front substrate 122 and the rear substrate 120 of this example, for example, polyimides are used as the base material. The acoustic impedance of the polyimides is approximately 3 Mrayl.

<Acoustic Matching Layer>

Next, the non-conductive acoustic matching layer 110 and the conductive acoustic matching layer 111 of the present embodiment are described with reference to FIG. 2 and FIG. 3. FIG. 2 is a schematic perspective view showing the layered body of the acoustic matching layer (111, 110) and the piezoelectrics 114 related to Embodiment 1. FIG. 3A is a schematic perspective view showing a first groove 110a, a second groove 110b, and the conductive, films 110c in the non-conductive acoustic matching layer 110 related to Embodiment 1. FIG. 3B is a schematic perspective view showing the resin 110d filling each of the first grooves 110a and the second grooves 110b of FIG. 3A.

The non-conductive acoustic matching layer 110 and the conductive acoustic matching layer 111 adjust the acoustic impedance between the piezoelectrics 114 and the subject. Therefore, the non-conducting acoustic matching layer 110 and the conductive acoustic matching layer 111 are arranged between the piezoelectrics 114 and the front substrate 122 (refer to FIG. 1). Moreover, a material with different acoustic impedance is respectively used in the non-conductive acoustic matching layer 110 and the conductive acoustic matching layer 111. This is performed in order to gradually change the acoustic impedance between the piezoelectrics 114 and the acoustic lens, and to achieve acoustic matching thereby. Moreover, a material allowing for the machining of metals is used in the non-conductive acoustic matching layer 110.

As the non-conductive acoustic matching layer 110, for example, machinable glass, machinable ceramics, a mixture of an epoxy and metal oxide powder, a mixture of epoxy and metal powder, etc., may be used. These allow for the machining of metals and have an acoustic impedance suitable for joining with the piezoelectrics 114. The acoustic impedance of the non-conductive acoustic matching layer 110 is approximately 9 to 15 Mrayl. Moreover, carbon (isotropic graphite and/or graphite) is an example of the material of the conductive acoustic matching layer 111. Carbon has an acoustic impedance suitable for arrangement between the non-conductive acoustic matching layer 110 and the front substrate 122. The acoustic impedance of the conductive acoustic matching layer 111 is approximately 4 to 7 Mrayl. Moreover, although the thickness of the conductive acoustic matching layer 111 (length of the front-back direction (z direction in FIG. 1)) depends on the frequency band used, the frequency band generally used for the abdomen is for example 150 μm to 200 μm.

Figure 2:
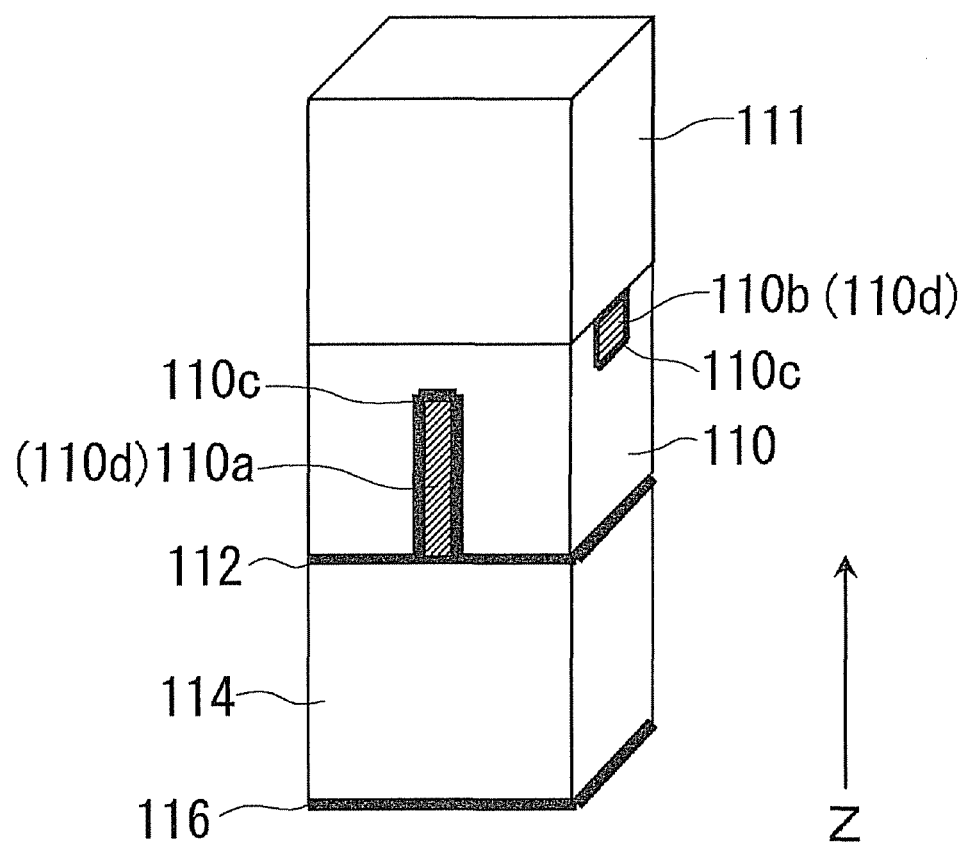
[FIG. 2] is a schematic perspective view showing the layer (lamination) stack of the acoustic matching layer and the piezoelectrics related to Embodiment 1.
Figure 3A:
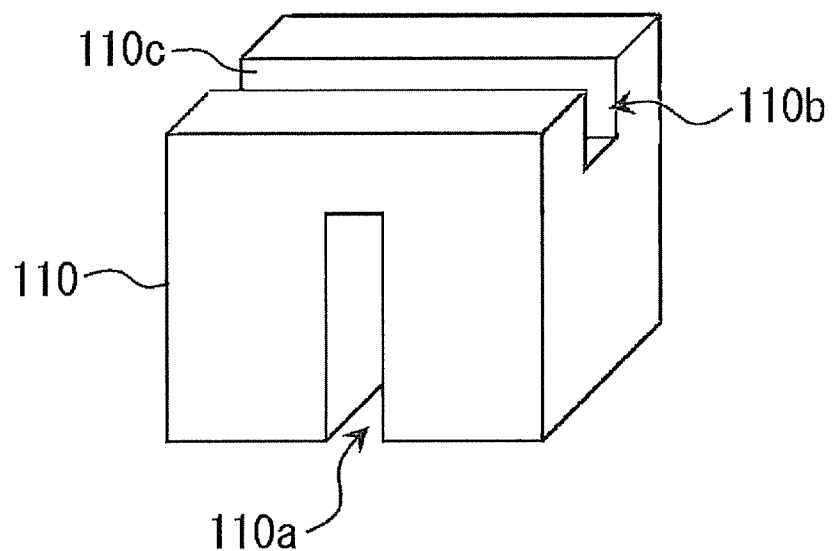
[FIG. 3A] is a schematic perspective view showing the groove in the non-conductive acoustic matching layer and the conductive film related to Embodiment 1.
Figure 3B:
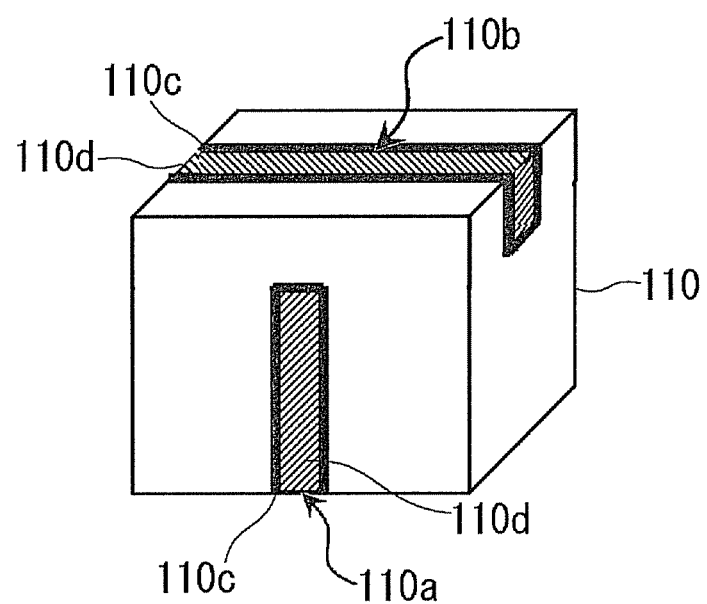
[FIG. 3B] is a schematic perspective view showing the resin filling of the first groove and the second groove of FIG. 3A, respectively.

As shown in FIG. 2 and FIG. 3A, the first grooves 110a are provided in a boundary surface between the front surface electrodes 112 of the non-conductive acoustic matching layer 110. Depth of the first grooves 110a reach the mid-way point of the non-conductive acoustic matching layer 110. Here, the boundary surface is the back surface of the non-conductive acoustic matching layer 110. Moreover, the mid-way point is the position between the back surface and the front surface of the non-conductive acoustic matching layer 110. In other words, the first grooves 110a are provided leading up to the mid-way point of the non-conductive acoustic matching layer 110 without penetrating the non-conductive acoustic matching layer 110. Moreover, the mid-way point is not necessarily equally distant from both the back surface and the front surface.

Moreover, the second grooves 110b are provided on the boundary surface with the conductive acoustic matching layer 111 of the non-conductive acoustic matching layer 110. The second grooves 110b reach the mid-way point (medial part) of the non-conductive acoustic matching layer 110, exceeding the edge of the front side of the first grooves 110a. The boundary surface is the front surface of the non-conductive acoustic matching layer 110. In other words, the second grooves 110b are provided leading further backwards than the front edge of the first grooves 110a in between the back surface and the front surface of the non-conductive acoustic matching layer 110. In other words, the second grooves 110b do not penetrate the non-conductive acoustic matching layer 110. Moreover, in an example of the depth of the first grooves 110a and the second grooves 110b of the non-conductive acoustic matching layer 110 of the present configuration, the length combining the depth of the first grooves 110a and the depth of the second grooves 110b is the thickness of the non-conductive acoustic matching layer 110 or more. Furthermore, the thickness of the non-conductive acoustic matching layer 110b is the length of the non-conductive acoustic matching layer 110 from the back surface to the front surface or more.

Moreover, as shown in FIG. 3A, the first grooves 110a are provided such that they reach from the side surface of the non-conductive acoustic matching layer 110 to the side surface of the opposite side. When described according to FIG. 3A, the first grooves 110a are provided by penetrating in the y direction of the non-conductive acoustic matching layer 110 array. Moreover, the second grooves 110b are provided such that they reach from the side surface without the first grooves 110a exposed to the side surface of the opposite side thereof in the non-conductive acoustic matching layer 110. When described according to FIG. 3A, the second grooves 110b are provided while penetrating in the x direction of the non-conductive acoustic matching layer 110, intersecting with the first grooves 110a. That is, as shown in FIG. 1, the first grooves 110a are provided by arranging in one direction in an element sequence direction with respect to each element comprising the non-conductive acoustic matching layer 110 arranged in a matrix state. Moreover, the second grooves 110b corresponding to this are provided by lining in a direction orthogonally intersecting the first grooves 110a with respect to each element.

Moreover, the one direction of the element array in which the first grooves 110a are arranged may be simply referred to as the "x direction" (refer to FIG. 1) in the following. The x direction in the element array corresponds to an example of "a first direction" in the following. Moreover, the direction in which the second grooves 110b are arranged, that is, the direction orthogonally intersecting the x direction, may be simply referred to as "y direction" (refer to FIG. 1) in the following.

Furthermore, the second grooves 110b lead up to the midway point of the non-conductive acoustic matching layer 110 exceeding the edge of the front side of the first grooves 110a from the front surface of the non-conductive acoustic matching layer 110. According to such a configuration, the first grooves 110a and the second grooves 110b intersect in the mid-way point of the non-conductive acoustic matching layer 110. As a result, a through hole 110e (refer to FIG. 6 and FIG. 7) is formed via the crossing part (intersection) of the first grooves 110a and the second grooves 110b (refer to symbol 110f of FIG. 7 to FIG. 9). The through hole 110e penetrates from the front surface to the back surface of the non-conductive acoustic matching layer 110. Moreover, the element array direction is a direction substantially perpendicular to the irradiation direction of ultrasonic waves of the ultrasonic transducer 100 (front-back direction (z direction of FIG. 1)). Moreover, the substantially orthogonal directions mentioned here are the x direction and y direction in FIG. 1 (refer to FIG. 1). Moreover, it is effective to provide the second grooves 110b shallower compared to the first grooves 110a. Moreover, when adopting a subdie, it is effective to adjust the position of the first grooves 110a to the subdie.

Figure 4:
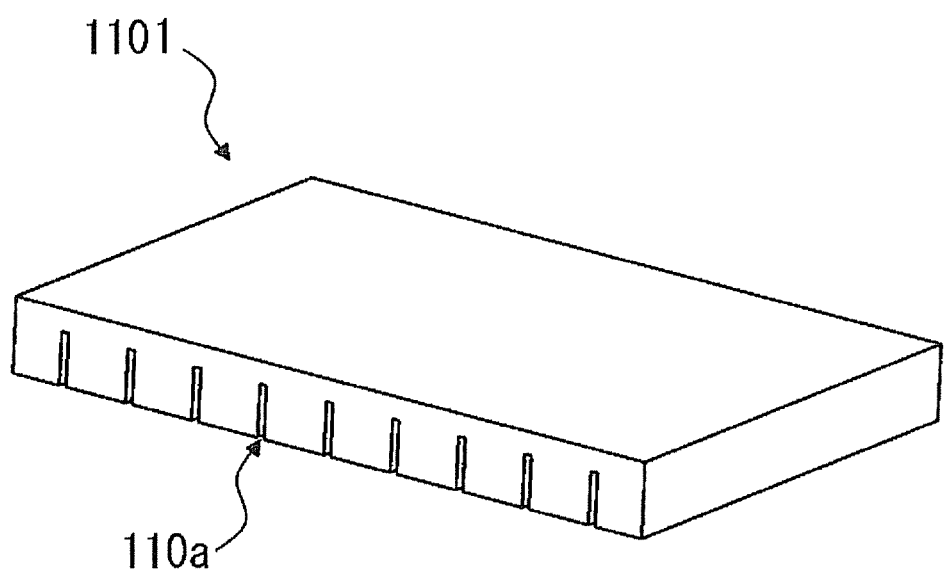
[FIG. 4] is a schematic perspective view showing a part of the manufacturing process of the non-conductive acoustic matching layer of the ultrasonic transducer related to Embodiment 1.
Figure 5:
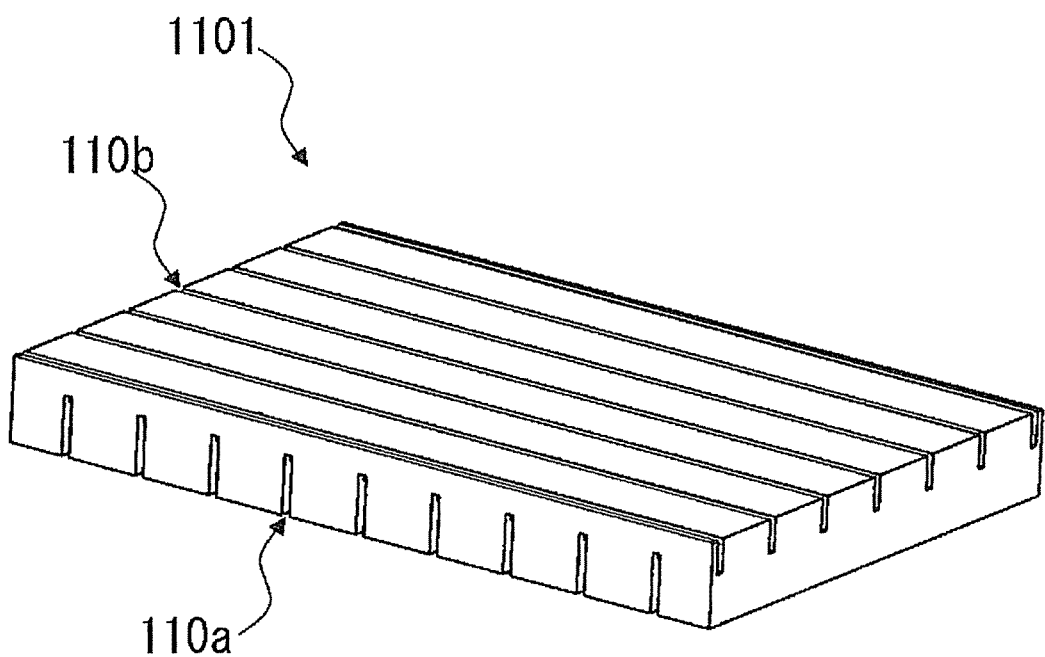
[FIG. 5] is a schematic perspective view showing the process following FIG. 4 within the manufacturing process of the ultrasonic transducer related to Embodiment 1.
Figure 7:
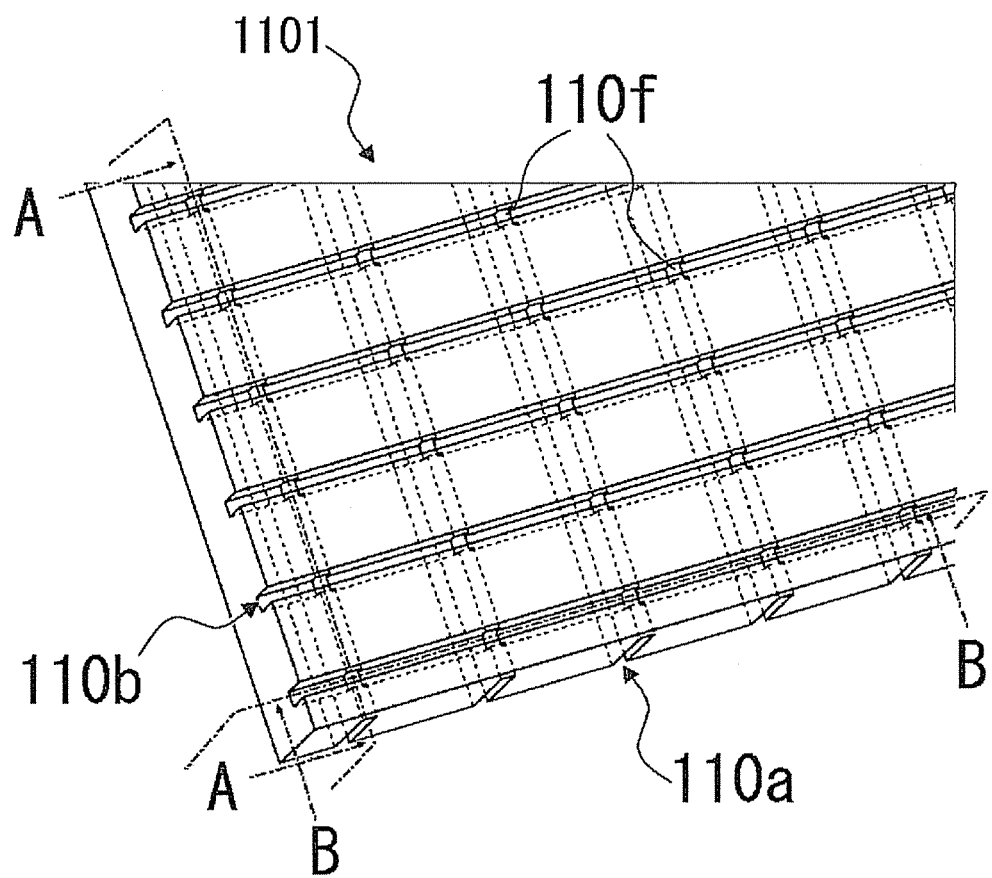
[FIG. 7] is a schematic perspective view showing the inner structure of the non-conductive material block of FIG. 6.

Furthermore, according to such a configuration, when providing a non-conductive acoustic matching layer 110 on the non-conductive acoustic matching layer 110, the first grooves 110a may be provided on each element belonging to one row in the element array with a single procedure (refer to FIG. 4, FIG. 5, and FIG. 7). In the same manner, according to the configuration of the second grooves 110b, the second grooves 110b may be provided on each element belonging to one row in the element array by a single procedure. Moreover, the grooves should be provided at once to each element (layered body) belonging to one row or one column, with other configurations possible. For example, the element located on both sides of the element array direction does not necessarily need to penetrate in the element array direction.

Moreover, on the inner surfaces of the first grooves 110a and the second grooves 110b in the non-conductive acoustic matching layer 110 shown in FIG. 3 (A), a conductive film 110c is provided throughout the entire surface thereof by plating, spattering, etc. The first grooves 110a are provided with the conductive film 110c up to the mid-way point of the non-conductive acoustic matching layer 110 from the back surface of the non-conductive acoustic matching layer 110 via a crossing part 110f. In other words, the conductive film 110c of the first grooves 110a becomes an electrical conductive path between the back surface of the non-conductive acoustic matching layer 110 and the crossing part 110f. Moreover, the conductive film 110c of the second grooves 110b becomes the electrical conductive path between the crossing part 110f and front surface of the non-conductive acoustic matching layer 110. Accordingly, the electrically conductive path via the through hole 110e is provided between the back surface of the non-conductive acoustic matching layer 110 and the back surface of the conductive acoustic matching layer 111. As a result, the front surface electrode 112 adjacent to the back surface of the non-conductive acoustic matching layer 110 is conducted with the wiring pattern of the front substrate 122 via the conductive film 110c provided in the through hole 110e and the conductive acoustic matching layer 111. Furthermore, the wiring pattern of the front substrate 122 comprises cases of electrode-plane.

Moreover, as shown in FIG. 3B, a resin 110d is filled further inside the first grooves 110a in the non-conductive acoustic matching layer 110 and the conductive film of the second grooves 110b in the conductive film 110c. An epoxy adhesive, etc., may be used as the resin 110d. By means of filling the first grooves 110a and the second grooves 110b with the resin 110d, effects from providing the first grooves 110a and the second grooves 110b on the non-conductive acoustic matching layer 110 may be suppressed. However, the configuration is not necessarily limited to the configuration of filling the resin 110d in the first grooves 110a and the second grooves 110b. That is, sometimes, the resin 110d does not need to be provided. For example, depending on the shape of the element (layered body) and/or the relationship with the vibration mode of the ultrasonic transducer 100, acoustic effects caused due to providing the first grooves 110a and the second grooves 110b in the acoustic matching layer are sometimes small. In such cases, the resin 110d does not need to be provided. Moreover, the resin may be provided in only one among the first grooves 110a and the second grooves 110b.

Moreover, the first grooves 110a and the second grooves 110b shown in FIGS. 1 to 3B are provided such that the depth direction thereof is parallel to the irradiation direction of the ultrasonic waves in the ultrasonic transducer 100 (front-back direction of the element (z direction of FIG. 1)). However, it is not necessarily limited to the configuration. For example, one or both of the first grooves 110a and the second grooves 110b may be provided by slanting towards the front-back direction of the element. Moreover, a case was described in which the conductive film 110c is provided throughout the entire inner surface of the first grooves 110a and the second grooves 110b; however, it is not necessarily limited to this case. The front surface electrode 112 and the conductive acoustic matching layer 111 may be conducted via the non-conductive acoustic matching layer 110 according to other configurations. For example, the conductive film 110c may be provided so as to pass from the edge of the back surface side of the non-conductive acoustic matching layer 110 to an area leading to the conductive acoustic matching layer 111. Moreover, not limited to the conductive film 110c, if a connecting lead may be provided to the through hole 110e, such a configuration of this kind may also be adopted.

Moreover, in the non-conductive acoustic matching layer 110 shown in FIG. 1, the first grooves 110a are arranged in the y direction alongside the x direction. Moreover, the second grooves 110b are provided in the x direction alongside the y direction. However, the configuration of the ultrasonic transducer 100 of the present embodiment is not limited to this. That is, the first grooves 110a may be provided in the x direction alongside the y direction, and the second grooves 110b may be provided in the y direction alongside the x direction.

Moreover, in the non-conductive acoustic matching layers 110 shown in FIG. 1 to FIG. 3B, one each of the first grooves 110a and the second grooves 110b are respectively provided in one element. However, it is not necessarily limited to this. For example, if at least one among the first grooves 110a and the second grooves 110b may be provided in plurality in one element, a configuration of this kind may also be adopted. Moreover, in the ultrasonic transducer 100 in FIG. 1, the piezoelectrics 114, non-conductive acoustic matching layer 110, conductive acoustic matching layer 111, front substrate 122, and the acoustic lens are arranged and layered in order from the rear to the front. However, without limiting to such a configuration, the acoustic matching layer may be three layers or more. For example, the non-conductive acoustic matching layer 110, conductive acoustic matching layer 111, and front substrate 122 may be arranged in order from the rear to the front, and furthermore, from the viewpoint of acoustic adjustment with the acoustic lens, the acoustic matching layer may be arranged on the front of the front substrate 122.

Moreover, by means of suppressing the groove widths of both the first grooves 110a and the second grooves 110b to a maximum of approximately 30% of the element width, the radiation performance of the ultrasonic pulse, the vibration mode of the ultrasonic transducer 100, the operation of providing a conductive film 110c, etc. become effective. If the element is, for example, 150 μm wide, it is approximately 50 μm to 10 μm. Here, "element" is the layered body of the piezoelectrics 114, non-conductive acoustic matching layer 110, and conductive acoustic matching layer 111 (refer to FIG. 2). Moreover, "element width" is the width of the element in the array direction of the first grooves 110a and the array direction of the second grooves 110b of the ultrasonic transducer 100 (for example, x direction or y direction of FIG. 1). Moreover, although the illustrated element has a substantially square-formed cross-section, not limited to this, the cross-section may be substantially rectangular.

<Acoustic Lens>

The acoustic lens (not illustrated) converges the transmitted and received ultrasonic waves and forms them into a beam shape. However, in the case of a 2D-array, focus may be three-dimensionally connected by the phase control of each element; therefore, a lens function is sometimes not added. As raw materials of the acoustic lens, silicone, etc., which comprises similar acoustic impedance with the living body, is used.

(Abstract of the Manufacturing Method of the Ultrasonic Transducer)

Next, the manufacturing method of the ultrasonic transducer 100 related to Embodiment 1 is described with reference to FIGS. 4 to 12. Specifically, the process of providing the first grooves 110a and the second grooves 110b in the non-conductive acoustic matching layer 110 is mainly described. FIG. 4, FIG. 5, and FIGS. 10 to 12 are schematic perspective views showing the manufacturing process of the ultrasonic transducer 100 related to Embodiment 1.

<<Forming the First Grooves/FIG. 4>>

Figure 12:
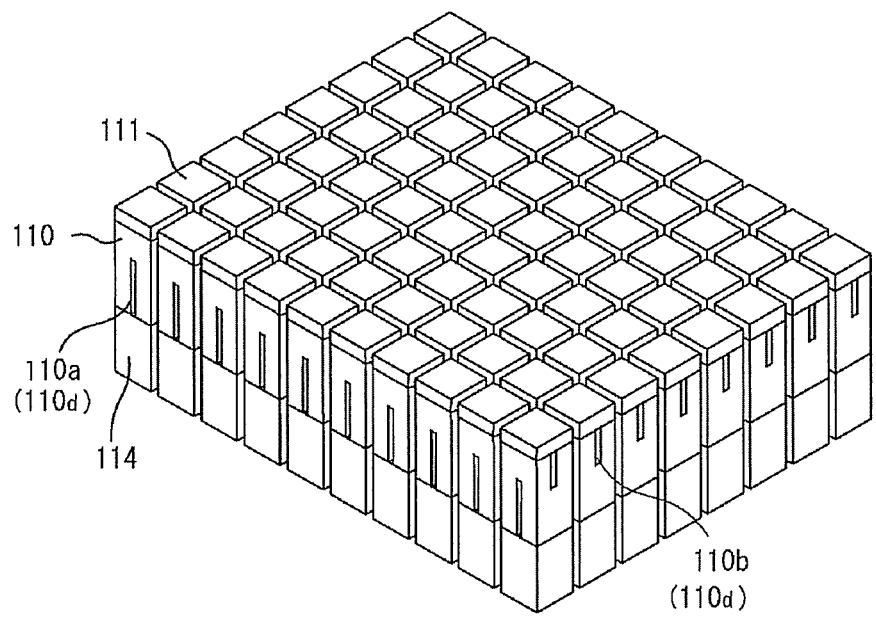
[FIG. 12] is a schematic perspective view showing the process following FIG. 11 within the manufacturing process of the ultrasonic transducer related to Embodiment 1.

As illustrated in FIGS. 1 to 3, the acoustic matching layer in the ultrasonic transducer 100 of the present embodiment is configured by layering the non-conductive acoustic matching layer 110 and the conductive acoustic matching layer 111. A non-conductive material block 1101 shown in FIG. 4 is used in forming the non-conductive acoustic matching layer 110 of the acoustic matching layer. In the same manner, a conductive material block 1111 is used in manufacturing the conductive acoustic matching layer (FIG. 10) 111. Moreover, the non-conductive material block 1101 and the conductive material block 1111 are as shown in FIG. 12 after they have been divided so that they may be two-dimensionally arrayed.

First, as shown in FIG. 4, with respect to the non-conductive material block 1101, the first grooves 110a are formed with a desired pitch in the y direction alongside the x direction (y direction in FIG. 1). The first grooves 110a are provided leading to the mid-way point of the non-conductive material block 1101 from the back surface of the non-conductive material block 1101. That is, it is provided up to the mid-way point between the back surface and the front surface of the non-conductive material block 1101 so as to prevent from penetrating the non-conductive material block 1101 in the front-back direction (depth).

Moreover, the first grooves 110a are provided in pluralities with a pitch corresponding to the element pitch of the ultrasonic transducer 100. In other words, when providing the first grooves 110a alongside the x direction of the element array, at least the number of first grooves 110a corresponding to the number of rows are provided. Moreover, when providing the first grooves 110a alongside the y direction of the element array, at least the number of first grooves 110a corresponding to the number of columns is provided. Moreover, the number of first grooves 110a in the acoustic matching layer block 1101 in FIG. 4, etc., is shown as a concept.

As mentioned above, for the first grooves 110a, cutting is provided in the non-conductive acoustic matching layer 110. The cutting width (width of the first grooves 110a) may be, for example, approximately 30% or less of the element width and 10 μm or more. As an example of the cut-in width to the element width under such circumstances, having a width of 50 μm for the element width of 350 μm may be considered. Moreover, the pitch of the cut-in width may be approximately 0.4 mm. Such a cut-in width is effective for the radiation performance of the ultrasonic pulse, the vibration mode of the ultrasonic transducer 100, and the formation process of the conductive film 110c.

<<Forming of the Second Groove/FIG. 5>>

As shown in FIG. 4, the second grooves 110b are provided along with or simultaneously with providing the first grooves 110a to the non-conductive material block 1101 (FIG. 5). The second grooves 110b are provided backwards from the front surface of the non-conductive material block 1101, to a location exceeding the edge of the front side of the first grooves 110a. Thereby, the second grooves 110b lead up to the mid-way point of the non-conductive acoustic matching layer 110. That is, it is provided such that the non-conductive acoustic matching layer 110 is not penetrated in the front-back direction. For example, it is provided in a position leading further backwards than the crossing part 110f located between the back surface and the front surface of the non-conductive acoustic matching layer 110 (refer to FIG. 8, FIG. 9).

Moreover, the second grooves 110b are provided in pluralities with a pitch corresponding to the element pitch of the ultrasonic transducer 100. In other words, when providing the second grooves 110b alongside the x direction of the element array, at least the number second grooves 110b corresponding to the number of rows are provided. Moreover, when providing the second grooves 110b alongside the y direction of the element array, at least the number of second grooves 110b corresponding to the number of columns are provided.

Figure 6:
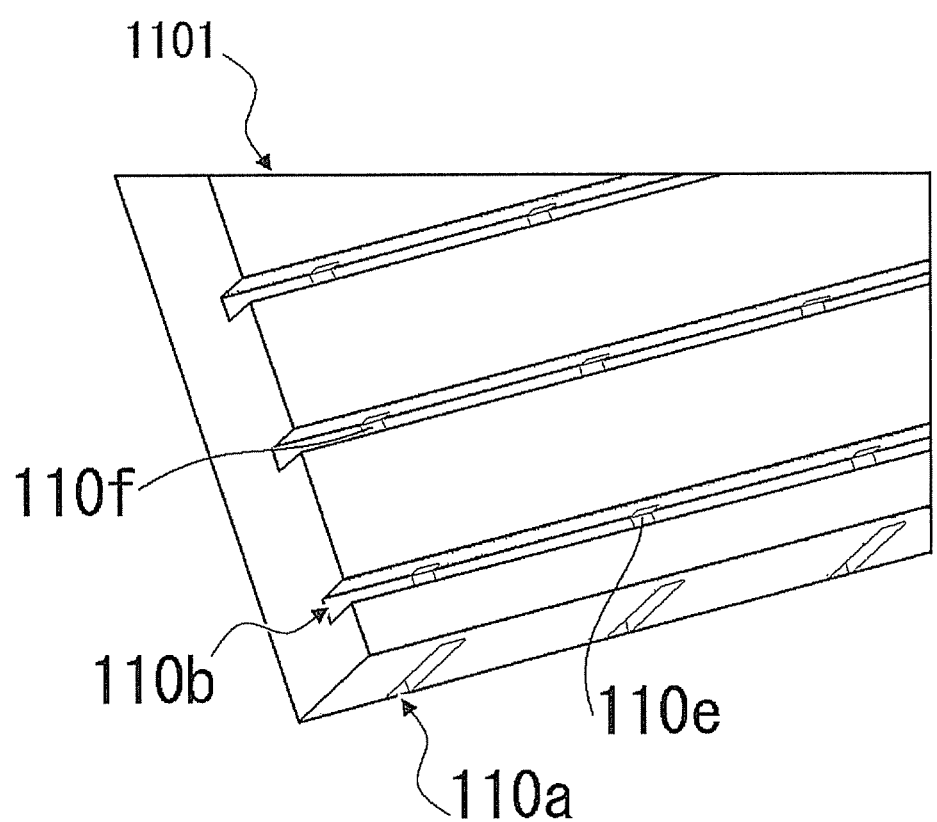
[FIG. 6] is a schematic perspective view showing the first grooves, second grooves, and the through hole of the non-conductive material block of FIG. 5.
Figure 8:
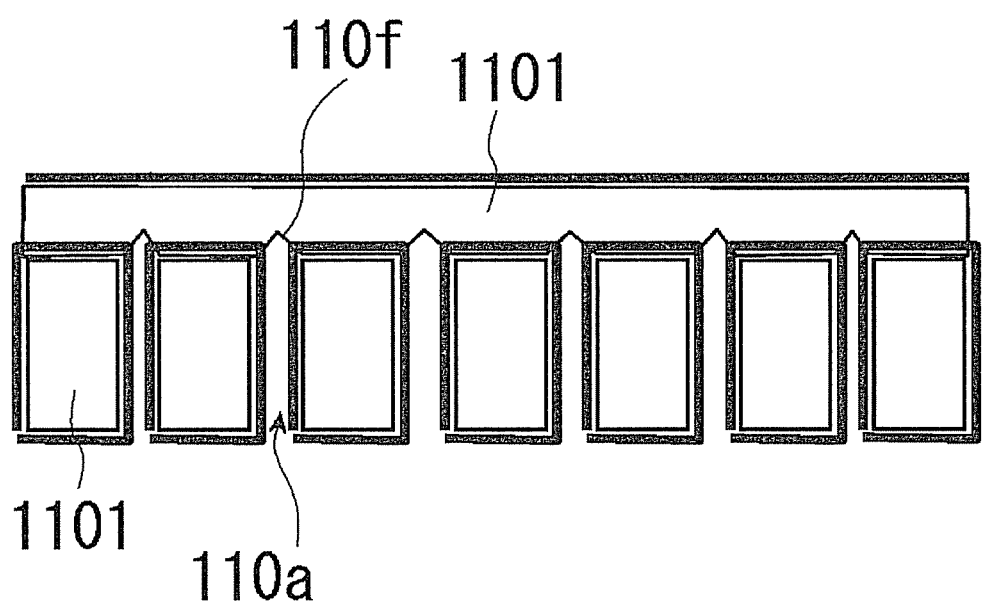
[FIG. 8] is an A-A cross-section of the non-conductive material block of FIG. 7.
Figure 9:
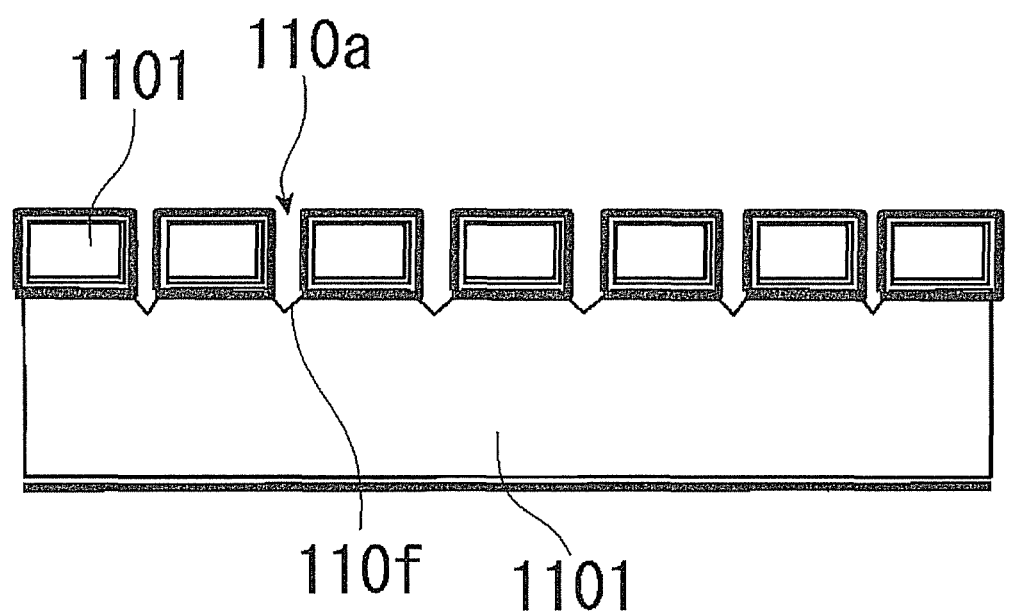
[FIG. 9] is a B-B cross-section of the non-conductive material block of FIG. 7.

Here, the crossing part 110f of the first grooves 110a and the second grooves 110b formed in the non-conductive material block 1101 as well as the through hole 110e are described with reference to FIGS. 6 to 9. FIG. 6 is a schematic perspective view showing the first grooves 110a, the second grooves 110b, and the through hole 110e of the non-conductive material block 1101 of FIG. 5. FIG. 7 is the schematic perspective view showing the inner configuration of the non-conductive material block 1101 of FIG. 6. FIG. 8 is the A-A cross-section view of the non-conductive material block 1101 shown in FIG. 7. FIG. 9 is the B-B cross-section view of the non-conductive material block 1101 shown in FIG. 7.

When the first grooves 110a and the second grooves 110b are formed, as shown in FIG. 6 and FIG. 7, the first grooves 110a and the second grooves 110b intersect each other. Moreover, due to the first grooves 110a and the second grooves 110b intersecting each other, the through hole 110e that passes from the front surface to the back surface of the non-conductive material block 1101 is formed. As shown in FIG. 8, in the cross-section along the second grooves 110b in the non-conductive material block 1101 (A-A cross-section of FIG. 7), the first grooves 110a are arranged with a predetermined pitch. Furthermore, as shown in FIG. 9, in the cross-section of the non-conductive material block 1101 orthogonally intersecting the cross-section of FIG. 8 (B-B cross-section of FIG. 7), the second grooves 110b are arranged with a predetermined pitch. The base of the first grooves 110a and second grooves 110b are connected in the area in which the first grooves 110a and the second grooves 110b intersect (crossing part 110f of FIG. 8, FIG. 9). Furthermore, as shown in FIG. 6 and FIG. 7, the crossing part 110f is formed in correspondence with the element pitch in the y direction and x direction.

Figure 10:
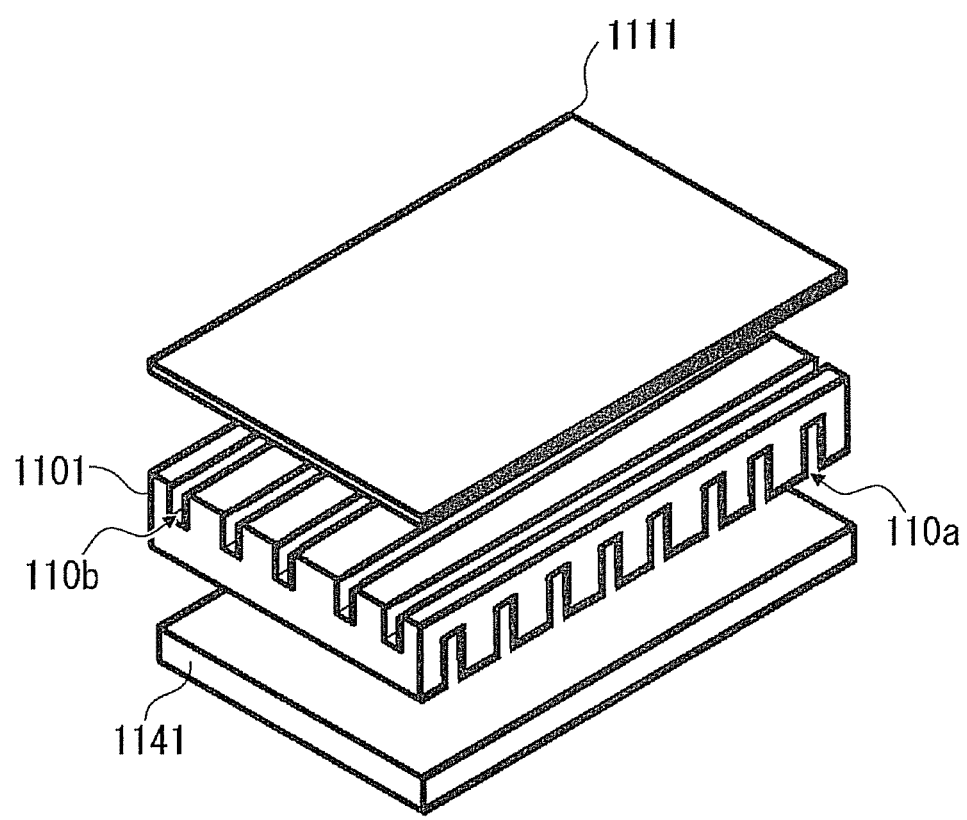
[FIG. 10] is a schematic perspective view showing the process following FIG. 5 within the manufacturing process of the ultrasonic transducer related to Embodiment 1.
Figure 11:
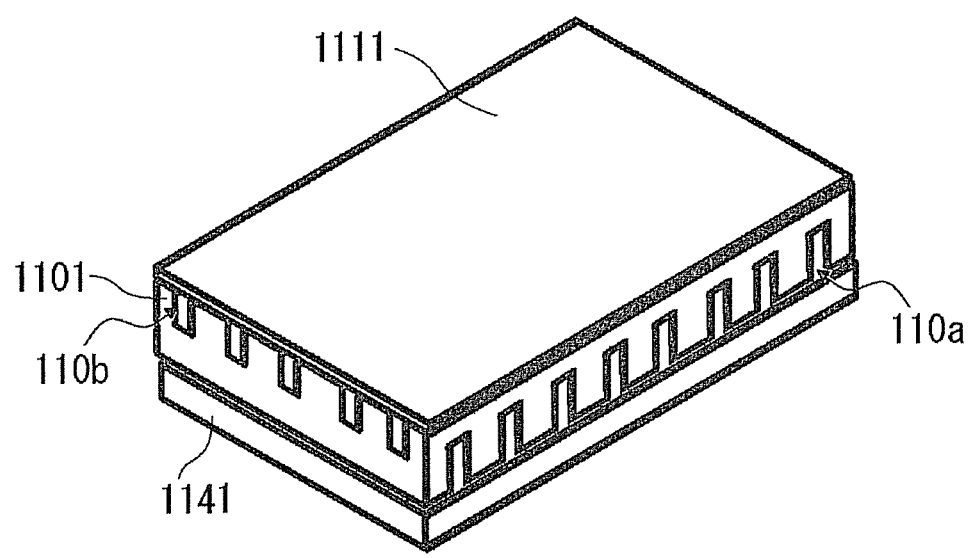
[FIG. 11] is a schematic perspective view showing the process following FIG. 10 within the manufacturing process of the ultrasonic transducer related to Embodiment 1.

In the subsequent process, the non-conductive material block 1101 is connected to the conductive material block 1111 and the piezoelectrics material block 1141 (FIG. 10. FIG. 11), thus forming the layered bodies. As mentioned above, by means of forming the first grooves 110a and the second grooves 110b with the predetermined pitch, each non-conductive acoustic matching layer 110 is provided with at least one or more through holes 110e when the layered bodies are divided in the xy direction (FIG. 12).

In providing the second grooves 110b, the cutting width (width of the second grooves 110b) may be approximately 30% or less of the element width and 10 µm or more in terms of the radiation performance of the ultrasonic pulse, the vibration mode of the ultrasonic transducer 100, and the formation process of the conductive film 110c. Moreover, regarding the order of providing the first grooves 110a and the second grooves 110b, either may come first or they may be simultaneous. Moreover, the number of the second grooves 110b in the non-conductive material block 1101 in FIG. 5, etc., is shown as a concept.

<<Conductive Film Forming>>

Next, the conductive film 110c is provided on the first grooves 110a and the second grooves 110b. The conductive film 110c is, for example, provided throughout the entire inner surface of the first grooves 110a and the second grooves 110b by plating, spattering, etc. At this time, the conductive film may also be provided on the front surface, back surface, side surface, etc., of the non-conductive material block. Thereby, the first grooves 110a and the second grooves 110b (through hole 110e) are electrically conducted from one end to the other. Moreover, one end to the other indicates from the back surface to the front surface of the non-conductive material block is indicated. Furthermore, the front surface electrode 112 adjacent to the back surface of the non-conductive acoustic matching layer 110 is electrically conducted with the wiring pattern of the front substrate 122 via the conductive film 110c and the conductive acoustic matching layer 111.

Moreover, the conductive film 110c does not necessarily have to be provided on the entire inner surface of the second grooves 110b and the front surface, back surface, and side surface of the non-conductive material block. For example, it may be a part of the side surface among the inner surfaces of the first grooves 110a and the second grooves 110b. That is, if the conductive film 110c may be provided such that it passes from one end of the first grooves 110a (edge of the back surface side) to the other end of the second grooves 110b (conductive acoustic matching layer 111 side), it does not need to be provided on the entire inner surface of the first grooves 110a and the second grooves 110b. That is, if an electrical connection may be ensured without fail from the front surface electrode 112 to the conductive acoustic matching layer 111, the conductive film 110c may be provided only on a part of the side surface leading from one end to the other end of the through hole 110e. Moreover, if the connecting lead may be provided from the front surface electrode 112 to the conductive acoustic matching layer 111 by passing the first grooves 110a and the second grooves 110b, the connecting lead may be provided instead of the conductive film 110c.

<<Resin Filling>>

After providing the conductive film 110c, a process may be conducted whereby the resin 110d is filled further inside the conductive film 110c on each of the first grooves 110a and the second grooves 110b. Whether or not to conduct this procedure is determined by the vibration design of the element. An epoxy adhesive, etc., may be used for the resin 110d; however, sometimes a silicone-based rubber adhesive is used. However, depending on the shape of the element and the vibration mode of the ultrasonic transducer 100, sometimes there is little acoustic effect due to the first grooves 110a and the second grooves 110b; in such cases, a resin 110d does not need to be provided. Furthermore, the element indicates the layered bodies of the piezoelectrics 114, non-conductive acoustic matching layer 110, and conductive acoustic matching layer 111. Moreover, the resin 110d may be provided on only one among the first grooves 110a and the second grooves 110b.

Moreover, regarding the order of providing the conductive film 110c and the resin 110d, this does not necessarily need to be conducted after providing both the first grooves 110a and the second grooves 110b. For example, after the first grooves 110a are provided, the conductive film 110c and the resin 110d are first provided from the first grooves 110a side before providing the second grooves 110b. The conductive film 110c and resin 110d may be subsequently provided in the second grooves 110b. However, the process mentioned above of simultaneously providing the conductive film 110c and the resin 110d after providing both the first grooves 110a and the second grooves 110b is easier as the manufacturing process of the ultrasonic transducer 100.

<<Block Connection/FIG. 10, 11>>

After the conductive film 110c is provided on the non-conductive material block 1101, or after the resin 110d is provided when there is a resin 110d, the non-conductive material block 1101 and the conductive material block 1111 are connected. That is, as shown in FIG. 10 and FIG. 11, the conductive material blocks 1111 are layered on the surface in which the edges of the second grooves 110b in the non-conductive material block 1101 are exposed, and then connected. Moreover, in the subsequent process, split grooves are provided in the xy direction to both the non-conductive material block 1101 and the conductive material block 1111, and thereby the number of layered bodies corresponding to the number of desired elements is formed, as shown in FIG. 12.

<<Piezoelectric Connection/FIG. 10, 11>>

After layering the non-conductive material block 1101 and the conductive material block 1111, the acoustic matching layer block thereof and a piezoelectrics material block 1141 are connected. That is, as shown in FIG. 10 and FIG. 11, the piezoelectrics material block 1141 is connected to the surface opposite to connection surface of the conductive material block 1111 in the non-conductive material block 1101. Furthermore, it is determined that the layer to become the front surface electrode 112 be provided in advance on the front surface of the piezoelectrics material block 1141. In the same manner, it is determined that the layer to become the back surface electrode 116 be provided in advance on the back surface of the piezoelectrics material block 1141. Moreover, the split grooves are provided in the piezoelectrics material block 1141 in the xy direction during the subsequent process, and are divided so that the desired number of elements of the piezoelectrics 114 in the ultrasonic transducer 100 is achieved (refer to FIG. 1). Furthermore, regarding the order of connecting the conductive material block 1111 and the piezoelectrics material block 1141 to the non-conductive material block 1101, either may come first.

<<Rear Substrate Connection>>

The rear substrate 120 is connected to the back surface of the back surface electrode 116 in the piezoelectrics 114. Thereby, the wiring pattern of the front substrate 122 is electrically conducted with each conductive acoustic matching layer 111. The wiring pattern may be the electrode-plane as a ground. Moreover, the wiring pattern of the rear substrate 120 and the back surface electrode 116 are electrically connected.

<<Split Groove Forming/FIG. 12>>

Next, the split grooves are provided in the xy direction to the layered bodies of the non-conductive material block 1101, conductive material block 1111, and piezoelectrics material block 1141. That is, as shown in FIG. 12, the split grooves are formed in a predetermined pitch in columns in the y direction along to the lamination direction of the acoustic matching layer block and the piezoelectric material block 1141, splitting the layered body of the block into blocks with a plurality of columns. Furthermore, the split grooves are provided in a predetermined pitch in rows in the x direction along the lamination direction of the acoustic matching layer block and the piezoelectric material block 1141. As a result, the element group is formed, the element group configuring a two-dimensional array of the layered body of the piezoelectrics 114, non-conductive acoustic matching layer 110, and conductive acoustic matching layer 111 as shown in FIG. 12 (the rear substrate 120, however, which is already connected and adhered, is not illustrated).

<<Backing Material Connection>>

After the elements are divided and the two-dimensional array is formed, a backing material 118 is connected to the back surface of the rear substrate 120. Moreover, regarding the configuration between the piezoelectrics 114, rear substrate 120, and backing material 118, without limitation to those shown in FIG. 1, structures such as an electrical circuit that process signals as necessary, a back surface matching layer, etc., may be interpositioned. However, the present backing adhering process may be conducted before the process of forming the split element grooves.

<<Front Substrate Connection>>

The front substrate 122 is connected on the front surface of the conductive acoustic matching layer 111 separated in the two-dimensional array. Thereby, the wiring pattern of the front substrate 122 and respective conductive acoustic matching layers 111 are electrically connected. The wiring pattern may be the electrode-plane as a ground.

<<Adding an Acoustic Matching Layer>>

If necessary, upon performance design, the acoustic matching layer may be further formed in front of the front circuit substrate 122.

<<Acoustic Lens Connection>>

After forming the configurations necessary upon design such as connecting the substrate to the front surface and back surface of the element group of the two-dimensional array, forming the additional acoustic matching layer, etc., the acoustic lens is formed or adhered to the very front surface of an oscillator as the final process. Furthermore, as mentioned above, when configuring the acoustic matching layer with three layers or more, the acoustic matching layer is arranged on the front surface of the front substrate 122 without adjoining the front substrate 122 and the acoustic lens. In this case, the acoustic lens is arranged on the further front surface of the acoustic matching layer located at the very front.

(Connection of the Ultrasonic Transducer and the External Device)

Next, an example of a connection configuration between the ultrasonic probe comprising the ultrasonic transducer 100 of Embodiment 1 and the ultrasonic diagnostic equipment body is described. Moreover, illustrations are omitted in the following description. The ultrasonic transducer 100 is provided inside the ultrasonic probe, comprising an interface (cable, etc.) in order to electrically connect the ultrasonic diagnostic equipment body and the ultrasonic probe. Moreover, the ultrasonic transducer 100 is electrically connected to the ultrasonic diagnostic equipment via a wiring pattern of the front substrate 122 (including a case of electrode-plane) and the interface of the rear substrate 120, and the interface of. The signals related to the transmitting and receiving of ultrasonic waves are alternately transmitted by the wiring pattern and interface.

Moreover, the circuit board provided with the electrical circuit such as the transmitter-receiver circuit, etc., may be provided inside the ultrasonic probe. Moreover, the connecting substrate connecting the interface and the electrical circuit may be provided inside the ultrasonic probe. In this case, the connecting substrate becomes the path through which transmitted and received, the interface connecting the ultrasonic probe and the body, the wiring pattern of the connecting substrate, and the circuit substrate are transmitted and received control unit of the ultrasonic diagnostic equipment body.

For example, the control unit of the ultrasonic diagnostic equipment body transmits electrical signals using the control of the drive of the ultrasonic transducer 100 to the ultrasonic probe via the interface. The electrical signals are transmitted to the electric circuit of the circuit board via the connecting substrate. The electric circuit applies voltage to the piezoelectrics 114 via the front substrate 122 and the rear substrate 120 based on signals from the control unit of the ultrasonic diagnostic equipment body. For example, voltage is applied to the back surface electrode 116 via the rear substrate 120. The front surface electrode 112 is connected to the ground via the first grooves 110a, the second grooves 110b, and the conductive acoustic matching layer 111 of the non-conductive acoustic matching layer 110 as well as the wiring pattern of the front substrate 122. Voltage is applied to the piezoelectrics 114 in this manner and ultrasonic pulses are transmitted to the test object.

Moreover, for example, when the ultrasonic transducer 100 receives reflected waves from the test object, the ultrasonic diagnostic equipment body transmits the electric signals converted by the piezoelectrics 114 to the electric circuit via the rear substrate 120, etc. Depending on the configuration, the electric signals converted by the piezoelectrics 114 are transmitted to the electric circuit via the non-conductive acoustic matching layer 110, conductive acoustic matching layer 111, front substrate 122, etc. The electric circuit performs predetermined processing (adding delays (phasing addition), amplifying, etc.) to the electric signals and furthermore, transmits the electric signals to the ultrasonic diagnostic equipment body via the connecting substrate and the interface. Based on the electric signals, ultrasonic images are produced on the ultrasonic diagnostic equipment body side.
(Function/Effect)

The function and effect of the ultrasonic transducer 100 and the ultrasonic probe related to Embodiment 1 described above are described.

As described above, in the ultrasonic transducer 100 of Embodiment 1, in the boundary surface (back surface of the non-conductive acoustic matching layer 110) between the front surface electrode 112 and the ultrasonic transducer 100 in each non-conductive acoustic matching layer 110, the first grooves 110a having depth leading up to the mid-way point are provided. Furthermore, in the non-conductive acoustic matching layer 110, the second grooves 110b having depth leading up to the mid-way point of the non-conductive acoustic matching layer 110 are provided on the boundary surface (front surface of the non-conductive acoustic matching layer 110) between the conductive acoustic matching layer 111 and the conductive acoustic matching layer 110. The mid-way point is, as mentioned above, a location further backwards than the front edge of the first grooves 110a. Moreover, the crossing part 110f is formed by the first grooves 110a and the second grooves 110b. As a result, as shown in FIG. 6 and FIG. 7, the through hole 110e leading from the boundary surface with the front surface electrode 112 to the boundary surface with the conductive acoustic matching layer 111 is formed. Furthermore, the conductive film 110c is provided so as to pass from at least the edge of the back surface side to the edge of the front surface of the non-conductive acoustic matching layer 110 (area leading to the back surface of the conductive acoustic matching layer 111) in the inner surface of the first grooves 110a and the second grooves 110b. In other words, the conductive film 110c is provided so as to pass from the rear edge of the first grooves 110a to the front edge of the second grooves 110b.

Consequently, by means of providing the first grooves 110a and the second grooves 110b in the non-conductive material block 1101, the conductive path may be formed on the non-conductive acoustic matching layer 110 by the process of forming the through hole 110e and the process of providing the conductive film 110c on the through hole 110e alone. Furthermore, the non-conductive material block 1101, conductive material block 1111, and piezoelectrics material block 1141 are layered in order to form the layered body. Subsequently, the split grooves are provided in the xy direction for the layered body, thereby forming the two-dimensional array of the element configured by comprising the layered body of the piezoelectrics 114, non-conductive acoustic matching layer 110, and conductive acoustic matching layer 111.

According to the ultrasonic transducer 100 manufactured by the manufacturing process, forming the conductive path of the non-conductive acoustic matching layer 110 may be made easier. Consequently, complication of the manufacturing process of the ultrasonic transducer 100 may be avoided. That is, the manufacturing process is simple if a configuration is achieved by providing the first grooves 110a, the second grooves 110b, and conductive film 110c in the non-conductive acoustic matching layer 110, and furthermore, the conductive path may be provided without fail from the front surface electrode 112 to the conductive acoustic matching layer 111.

[Embodiment 2]

Figure 13:
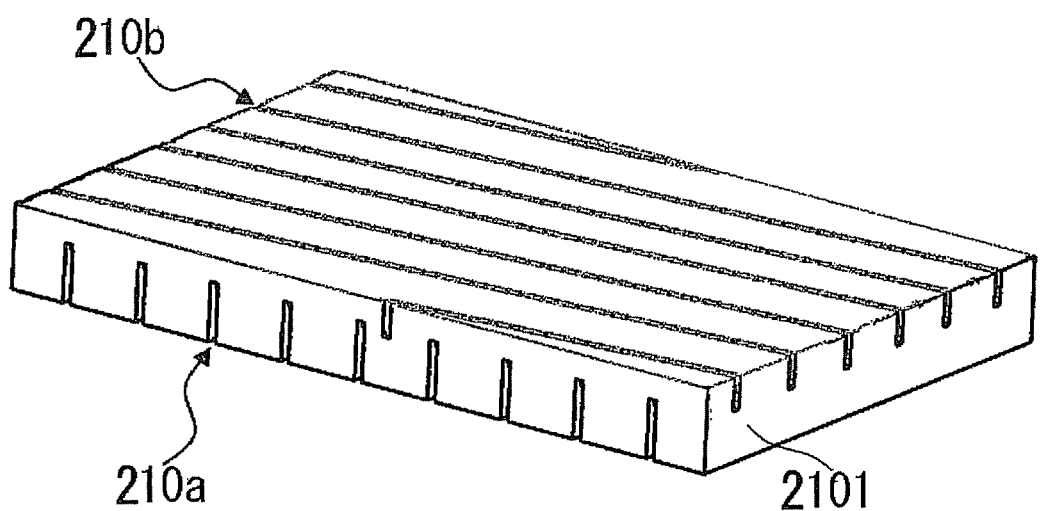
[FIG. 13] is a schematic perspective view showing a part of the manufacturing process of the non-conductive acoustic matching layer of the ultrasonic transducer related to Embodiment 2.

Next, the ultrasonic probe related to Embodiment 2 and the ultrasonic probe provided with the ultrasonic transducer are described with reference to FIGS. 13 to 17. FIG. 13 is a schematic perspective view showing the abstract of a non-conductive material block 2101 of the ultrasonic transducer related to Embodiment 2. Furthermore, areas differing from Embodiment 1 are mainly described in Embodiment 2, descriptions of other overlapping areas sometimes omitted. Moreover, the number of first grooves 210a and second grooves 210b in the non-conductive material block 2101 shown in FIG. 13 are shown as a concept.
(Schematic Configuration of the Ultrasonic Transducer)

In the ultrasonic transducer related to Embodiment 2 as well, the piezoelectrics are two-dimensionally arranged on the xy surface. The front surface electrode is arranged on each of the front surface side of the piezoelectrics, while the back surface electrode is provided on each of the back surface side of the piezoelectrics. Moreover, the non-conductive acoustic matching layer 210 (refer to FIG. 14, FIG. 16, etc.) is provided in correspondence with each front surface of the respective piezoelectrics. Furthermore, the conductive acoustic matching layer, front substrate, and acoustic lens are provided in order towards the front surface in front of the non-conductive acoustic matching layer 210. Moreover, the backing material is provided on the back side of the piezoelectrics. The rear substrate is provided between the backing material and the piezoelectrics.
(Configuration of the Non-conducting Acoustic Matching Layer and the Second Groove)

Figure 14:
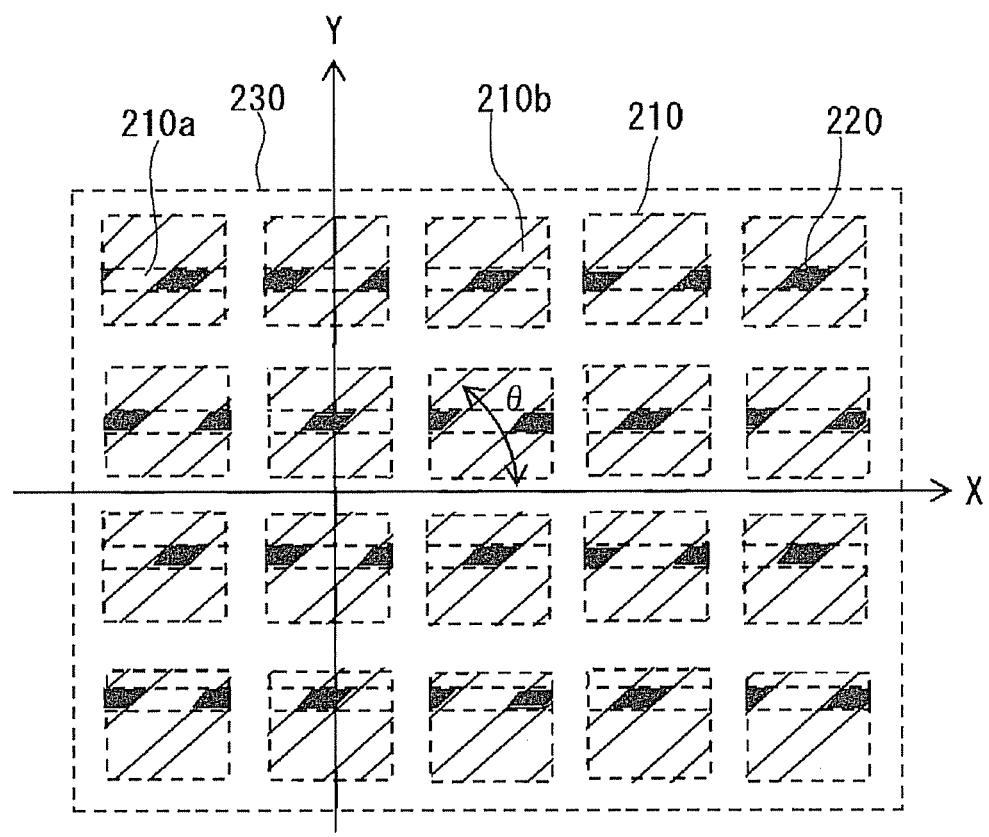
[FIG. 14] is a schematic perspective view showing the outline of an example of the second grooves formed on the non-conductive acoustic matching layer related to Embodiment 2.
Figure 15:
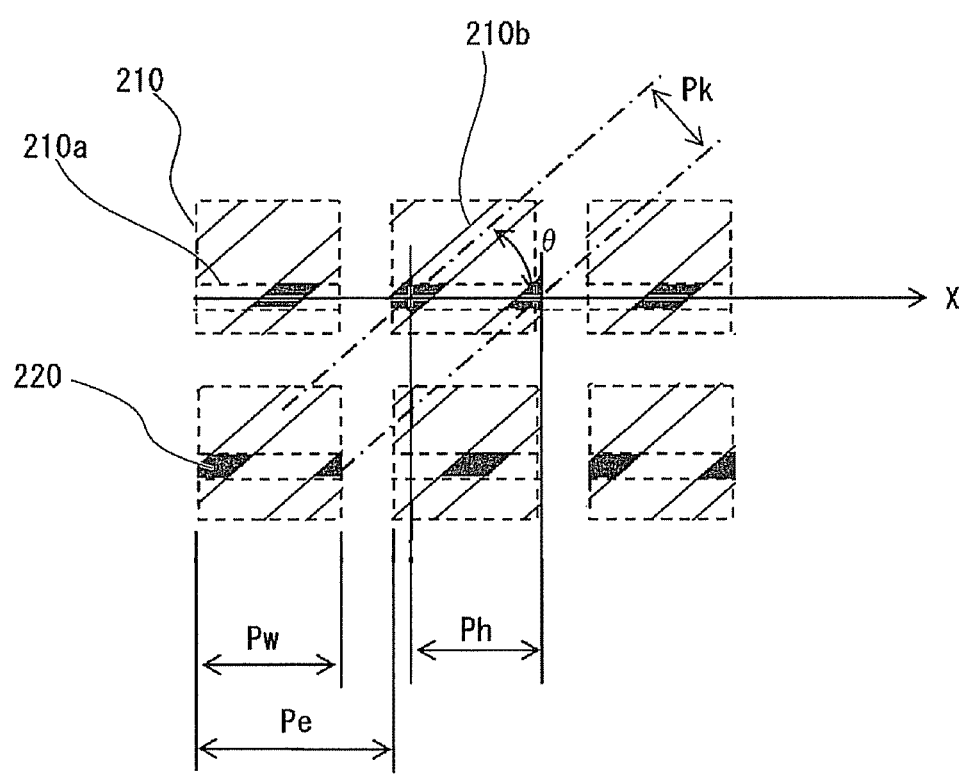
[FIG. 15] is a schematic enlarged view of a part of FIG. 14.

Next, the non-conductive acoustic matching layer 210, the first grooves 210a, and the second grooves 210b in the ultrasonic transducer of Embodiment 2 are described with reference to FIGS. 13 to 17. FIG. 14 is a top schematic perspective view of the non-conductive acoustic matching layer 210 related to Embodiment 2, and shows an abstract of an example of the second grooves 210b provided in the non-conductive acoustic matching layer 210. A non-conductive acoustic matching layer group 230 in the figure shows the entire two-dimensional array element arrangement of the non-conductive acoustic matching layer 210 in the figure as one conceptual bundle with dashed lines as a concept. Moreover, the crossing part 220 is the area in which the first grooves 210a parallel to the element array (x direction in the figure) and the second grooves 210b running diagonally towards the element array intersect. That is, the crossing part 220 shows the through hole formed in the non-conductive acoustic matching layer 210. Furthermore, in FIG. 14, among the plurality of two-dimensionally arranged non-conductive acoustic matching layers 210, only a part of the non-conductive acoustic matching layer 210 is shown. FIG. 15 is the schematic enlarged view of a part of FIG. 14.

[Groove Depth]

In Embodiment 2 as well, the conductive path electrically connecting from the front surface electrode to the conductive acoustic matching layer are formed by the first grooves 210a and the second grooves 210b (refer to FIG. 13) in the same manner as Embodiment 1. The first grooves 210a are provided in the back surface of the non-conductive acoustic matching layer 210, the first grooves 210a having depth leading up to the mid-way point. Moreover, the second grooves 210b are provided in the front surface of the non-conductive acoustic matching layer 210. The second grooves 210b lead up to the mid-way point. The mid-way point indicates the location further backwards than the front edge of the first grooves 210a. The crossing part 220 of the first grooves 210a and the second grooves 210b being formed, as a result, the through hole leading from the boundary surface with the front surface electrode of the piezoelectrics in the non-conductive acoustic matching layer 210 to the boundary surface with the conductive acoustic matching layer is formed.

[Groove Direction (Angle of the Groove)]

Moreover, in the same manner as Embodiment 1, the first grooves 210a of Embodiment 2 are provided in the y direction by penetrating towards the x direction with respect to the non-conductive acoustic matching layer 210 arranged in a matrix state. That is, the first grooves 210a are formed by penetrating in the x direction of the array of the non-conductive acoustic matching layer 210 so as to lead from the side surface of the non-conductive acoustic matching layer 210 to the side surface of the opposite side.

Whereas, the second grooves 210b of Embodiment 2 are, as shown in FIG. 14, provided such that they are slanted towards the array direction of the non-conductive acoustic matching layer 210 (for example, x direction) by a predetermined angle. Moreover, the second grooves 210b are provided so as to intersect the first grooves 210a. The inclination angle of the second grooves 210b is set to, for example, less than 90°. The inclination angle is the angle at which the second grooves 210b are slanted in the x direction in the two-dimensionally arranged non-conductive acoustic matching layer 210. The angle is established in order to provide the second grooves 210b so as to intersect the first grooves 210a. Furthermore, the inclination angle is the smaller angle among the angles configured by the array direction (for example, x direction) and the second grooves 210b (for example, θ in FIG. 14).

When the inclination angle of the second grooves 210b is 0°, sometimes the second grooves 210b and the first grooves 210a become parallel. When the second grooves 210b and the first grooves 210a become parallel, sometimes the non-conductive acoustic matching layer 210 is separated in small strips. Consequently, the angle configured by the groove 210a and the groove 210b is preferably approximately 30° to 90°.

Moreover, the second grooves 210b are formed by penetrating from one end to the other of the non-conductive acoustic matching layer 210.

In Embodiment 2 as well, the first grooves 210a may be provided by a single process to the non-conductive acoustic matching layer with respect to each element belonging to one column in the element array (refer to FIG. 13). In the same manner, the second grooves 210b may also be provided by a single process with respect to each of the plurality of elements in the element array. Moreover, the elements are arranged in a direction substantially perpendicular to the front-back direction of the ultrasonic transducer (refer to the z direction of FIG. 1). Moreover, the grooves should be provided at once to each of the plurality of elements, though other configurations are possible. For example, the element located on both sides of the element array direction (layered body) does not necessarily need to penetrate in the element array direction.

[Groove Pitch]

The second grooves 210b of Embodiment 2 are provided by slanting for the element array. Next, examples of the pitch between the second grooves 210b (a groove pitch) are described with reference to FIGS. 14 to 17. Moreover, the pitch between the second grooves 210b, that is, the groove pitch, indicates the distance from the halfway line of one of the second grooves 210b to the halfway line of the adjacent second groove 210b (refer to FIG. 15). That is, this shows the distance from the center of one of the second grooves 210b to the center of the adjacent second groove 210b. Moreover, for convenience of explanation, the groove pitch of the second grooves 210b may simply be referred to as "$Pk_2$", "$Pk_4$", "$Pk_6$", or "$Pk_8$" in the following explanation. Moreover, for convenience of explanation, the groove pitch of the first grooves 210a may simply be referred to as "$Pk_1$", "$Pk_3$", "$Pk_5$", or "$Pk_7$". Moreover, for convenience of explanation, the pitch of the through hole formed in the crossing part 220 of the first grooves 210a and the second grooves 210b may be referred to as "Ph." The Ph is, for example, the pitch of the through hole in the x direction in FIG. 15.

Moreover, the element width in one of the non-conductive acoustic matching layers 210 may simply be referred to as "Pw". That is, PW is the length in the array direction of the non-conductive acoustic matching layer 210 (for example, x direction in FIG. 15). In other words, Pw is the length from one side surface of the non-conductive acoustic matching layer 210 to the side surface of the opposite side. In the example of FIG. 15, "Pw" is the element width in the x direction.

Moreover, FIG. 15 shows the arrangement of the non-conductive acoustic matching layer 210 corresponding with a piezoelectric element sequence in the matrix state. For example, the periodic distance from the left edge of the non-conductive acoustic matching layer 210 in the x direction of FIG. 15 to the left edge of the adjacent element may simply be referred to as "Pe". In other words, Pe is the length from the center of the width distance of one of the non-conductive acoustic matching layers 210 to the center of the adjacent non-conductive acoustic matching layer 210 (element pitch). That is, Pe is the length that combines an element interval of the non-conductive acoustic matching layer 210 and the element width Pw. Moreover, the element interval mentioned here refers to the length from the right edge of the width direction of one of the non-conductive acoustic matching layers 210 to the left edge widthwise of the adjacent on-conductive acoustic matching layer 210.

Moreover, among the inclining angles of the second grooves 210b, the smaller angle may simply be referred to as "θ" Here, the inclining angle refers to the angle configured by the array direction of the element (for example, x direction) and the second grooves 210b.

<Groove Pitch Example 1>

The groove pitch $Pk_6$ of the second grooves 210b of Embodiment 2 may be set as the element width Pw or less, as shown in FIG. 15.

<Groove Pitch Example 2>

The groove pitch $Pk_2$ of the second grooves 210b of Embodiment 2 may be set as equal to or less than the element width Pw; furthermore, as illustrated in FIG. 15, the relationship between Pk and Pw may be established using the formula (1) below.

[Formula 1]

$$Ph = Pk_2/\sin\theta \leq Pw \tag{1}$$

Regarding each of the non-conductive acoustic matching layers 210, at least one or more through holes must be established as the conductive path in the front-back direction of the ultrasonic transducer (refer to the z direction of FIG. 1). According to the "groove pitch example 1" mentioned above, the through hole may be formed without particular hindrance even if the second grooves 210b are inclined towards the array direction x. Moreover, according to the "groove pitch example 2," establishing the groove pitch Pk for further forming the through hole in the non-conductive acoustic matching layer 210 becomes easier. Moreover, by means of setting the range of the degree of "θ" to greater than 30° and less than 90° (30°<θ<90°), establishment of the groove pitch Pk becomes much easier (in the first embodiment, θ is equivalent to 90°).

Figure 16:
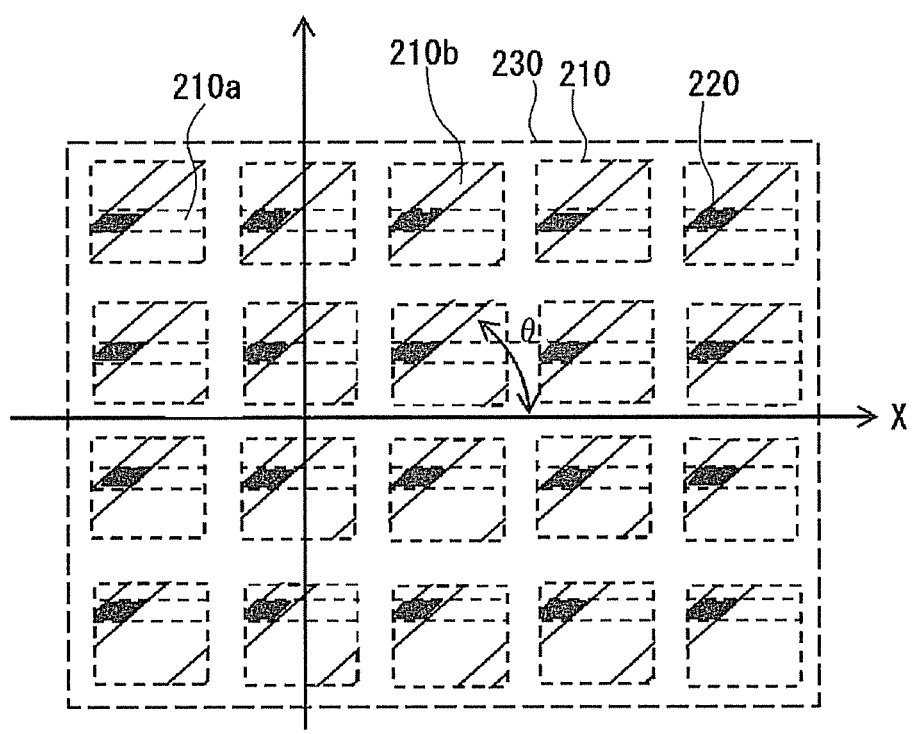
[FIG. 16] is a top schematic perspective view of the non-conductive acoustic matching layer showing the outline of another example of the second grooves formed on the non-conductive acoustic matching layer related to Embodiment 2.
Figure 17:
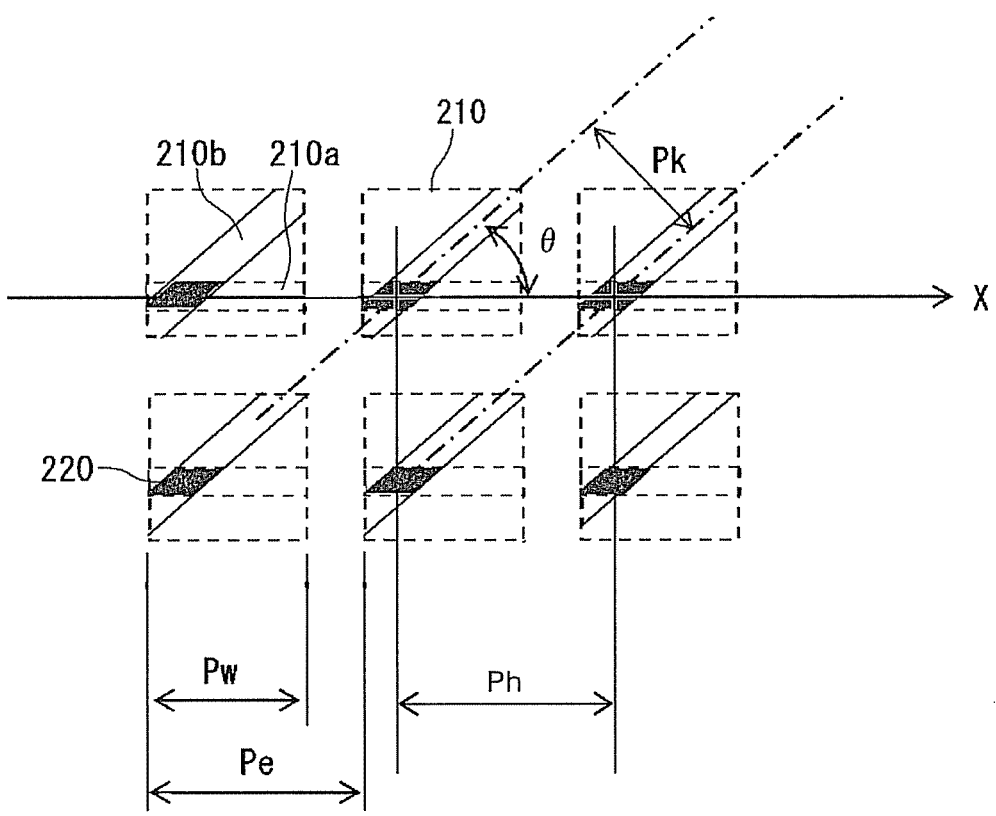
[FIG. 17] is a schematic enlarged view of a part of FIG. 16.

Next, another example of the groove pitch Pk is described with reference to FIG. 16 and FIG. 17. FIG. 16 is a top schematic perspective view of the non-conductive acoustic matching layer 210 related to Embodiment 2, showing another example of the second grooves 210b provided in the non-conductive acoustic matching layer 210. The non-conductive acoustic matching layer group 230 indicated by dashed lines in the figure shows the entire two-dimensional array element sequence of the non-conductive acoustic matching layer 210 in the figure as one conceptual bundle with dashed lines. FIG. 17 is the schematic enlarged view of a part of FIG. 16.

<Groove Pitch Example 3>

As illustrated in FIG. 16, the groove pitch $Pk_8$ of the second grooves 210b of Embodiment 2 may be set equally with the element pitch Pe. However, this includes accidental errors during the manufacturing process.

<Groove Pitch Example 4>

As illustrated in FIG. 17, the groove pitch $Pk_4$ of the second grooves 210b of Embodiment 2 may be set as in the following formula (2) regarding the relationship with the element pitch Pe. However, this includes accidental errors during the manufacturing process.

[Formula 2]

$$Ph = Pk_4/\sin\theta = Pe \tag{2}$$

In the same manner as the "groove pitch example 1" mentioned above, according to the "groove pitch example 3," even if the second grooves 210b are inclined towards the array direction x, the fear of forming of the through hole being affected due to the relationship with the first grooves 210a may be avoided. Moreover, in the same manner as the "groove pitch example 2," according to the "groove pitch example 4," establishing the groove pitch Pk for further forming of the through hole in the non-conductive acoustic matching layer 210 becomes easier. Moreover, by means of setting the range of the degree of "θ" to greater than 30° and less than 90° (30°<θ<90°), establishment of the groove pitch Pk becomes much easier.

[Conductive Path of the Non-conductive Acoustic Matching Layer]

Moreover, the first grooves 210a and the second grooves 210b in the non-conductive acoustic matching layer 210, a conductive film is provided throughout the entire surface thereof by plating, spattering, etc. This point is the same as in Embodiment 1. The through hole formed by the first grooves 210a, the second grooves 210b, and the crossing part 220 thereof leads from the back surface of the non-conductive acoustic matching layer 210 to the front surface (back surface of the conductive acoustic matching layer 111). Furthermore, in the through hole formed by the first grooves 210a, the second grooves 210b, and the crossing part 220 thereof, the conductive film 210c is provided in succession from at least one end of the through hole to the other end. That is, the edge of the front surface side to the edge of the back surface side (back surface of the conductive acoustic matching layer) is electrically conducted. As a result, the front surface electrode is conducted with the conductive acoustic matching layer adjacent to the front surface of the non-conductive acoustic matching layer 210 via the non-conductive acoustic matching layer 20. Furthermore, the front surface electrode is conducted with the wiring pattern of the front substrate via the non-conductive acoustic matching layer and the conductive acoustic matching layer.

Moreover, in Embodiment 2 as well, resin is filled further on the inner surfaces of the first grooves 210a in the non-conductive acoustic matching layer 210 and the conductive film of the second grooves 210b. Depending on the shape of the element (layered body) and/or the vibration mode of the ultrasonic transducer, the acoustic effects caused due to providing the first grooves 210a and the second grooves 210b in the acoustic matching layer 210 are sometimes small. That is, in such cases, the resin does not need to be provided. Moreover, the resin may be provided in only one among the first grooves 210a and the second grooves 210b.

Furthermore, another configuration may be taken as long as the front surface electrode and the conductive acoustic matching layer are conducted. For example, the conductive path may be provided to the through hole alone such that it passes from the edge of the front surface side to the edge of the back surface side of the non-conductive acoustic matching layer 210 among the inner surfaces of the first grooves 210a and the second grooves 210b. Moreover, if the connecting lead may be provided, a configuration of this kind may also be adopted. This is the same as in Embodiment 1.

[Other Examples]

Moreover, regarding the non-conductive acoustic matching layer 210 mentioned above, the first grooves 210a are provided in parallel to the array direction, and the second grooves 210b are provided so as to incline with the array direction x. However, the configuration is not limited to these as the ultrasonic transducer 100 of Embodiment 2. For example, the first grooves 210a may incline in the array direction and the second grooves 210b may be provided in parallel with the array direction y.

<Groove Pitch Example 5>

When inclining the first grooves 210a in the array direction in Embodiment 2 as mentioned above, the groove pitch $Pk_5$ may be established as equal to or less than the element width Pw.

<Groove Pitch Example 6>

When inclining the first grooves 210a in the array direction in Embodiment 2, the groove pitch $Pk_1$ of the first grooves 210a may be set as in the following formula (3) regarding the relationship with the element pitch Pe. However, this includes accidental errors during the manufacturing process.

[Formula 3]

$$Ph = Pk_1/\sin\theta \leq Pw \tag{3}$$

<Groove Pitch Example 7>

As illustrated in FIG. 16, the groove pitch $Pk_7$ of the second grooves 210b of Embodiment 2 may be set equally with the element pitch Pe. However, this includes accidental errors during the manufacturing process.

<Groove Pitch Example 8>

Moreover, when inclining the first grooves 210a in the array direction in Embodiment 2, the groove pitch $Pk_3$ of the first grooves 210a may be set as in the following formula (4) regarding the relationship with the element pitch Pe. However, this includes accidental errors during the manufacturing process.

[Formula 4]

$$Ph = Pk_3/\sin\theta = Pe \qquad (4)$$

Regarding each of the non-conductive acoustic matching layers 210, at least one or more through holes must be established as the conductive path in the front-back direction of the ultrasonic transducer (refer to the z direction of FIG. 1). According to the "groove pitch example 5" and the "groove pitch example 7" mentioned above, the fear of forming of the through hole being affected due to the relationship with the first grooves 210a may be avoided even if the second grooves 210b are inclined towards the array direction x. Moreover, according to the "groove pitch example 6" and the "groove pitch example 8," establishing the groove pitch Pk for further forming the through hole in the non-conductive acoustic matching layer 210 becomes easier. Moreover, by means of setting the range of the degree of "θ" to greater than 30° and less than 90° (30°<θ<90°), establishment of the groove pitch Pk becomes much easier.

Moreover, there may be three or more acoustic matching layers and, for example, the acoustic matching layer may be provided in front of the front substrate.

Moreover, the optimal width of the first grooves 210a and the second grooves 210b (array direction length) is the same as in Embodiment 1, so explanations are omitted.

(Abstract of the Manufacturing Method of the Ultrasonic Transducer)

Next, with reference to FIG. 13, the manufacturing method of the ultrasonic transducer related to Embodiment 2 is described. Particularly, the procedure of providing the first grooves 210a and the second grooves 210b of the non-conducting acoustic matching layer 210 is primarily described.

<<Forming the First Grooves>>

A non-conductive material block 2101 is also used in making the acoustic matching layer 210 in the ultrasonic transducer of Embodiment 2. Regarding the method of the manufacturing process of the ultrasonic transducer of Embodiment 2, first, as shown in FIG. 13, the first grooves 210a are provided with a predetermined pitch in the y direction alongside the x direction with respect to the non-conductive material block 2101. Moreover, the x direction and y direction mentioned here are the element array directions after the blocks are two-dimensionally split. The first grooves 210a are provided such that they reach from the back side of the non-conductive material block 2101 to the mid-way point of the block thickness. That is, it is provided leading up to the mid-way point between the back surface and the front surfaces in the non-conductive material block 2101 such that the non-conductive material block 2101 is not penetrated.

Moreover, in the same manner as Embodiment 1, if the first grooves 210a are arranged in parallel to the x direction of the element array, at least the number corresponding to the number of rows is formed. Moreover, when arranging the first grooves 210a in parallel with the y direction, at least the number corresponding to the number of columns is formed. Moreover, the number of first grooves 210a of the non-conductive material block 2101 in FIG. 13 is conceptually shown.

As an example of the cut-in width of the first grooves 210a, that is, the width of the first grooves 210a, it may be approximately 30% or less of the element width and 10 μm or more.

Under such conditions, for example, when the element width is 350 μm, having a cut-in width of 50 μm may be considered. Moreover, the pitch of the cut-in width may be approximately 0.4 mm. If such a cut-in width may be achieved, it is effective for the radiation performance of the ultrasonic pulse, the vibration mode of the ultrasonic transducer, and the formation process of the conductive film.

<<Forming the Second Grooves/FIG. 13>>

Next, the second grooves 210b as shown in FIG. 13 are provided in the non-conductive material block 2101. The second grooves 210b are provided leading from the front surface to the mid-way point of the non-conductive material block 2101. The mid-way point is any position in the non-conductive acoustic matching layer 210 that exceeds the edge of the front side of the first grooves 210a backwards, leading up to the back side of the non-conductive acoustic matching layer 210. That is, the second grooves 210b are provided further backwards than the crossing part 220 of the first grooves 210a between the back surface and the front surface in the non-conductive material block 2101 so as not to penetrate the non-conductive material block 2101.

Moreover, the second grooves 210b are provided in pluralities in a predetermined pitch with respect to the non-conductive material block 2101. Moreover, the second grooves 210b are provided by slanting towards the array direction x (refer to FIG. 14, etc.) with respect to non-conductive material block 2101 at a predetermined angle. Moreover, the array direction x is the array direction of the non-conductive acoustic matching layer 210 when the block is two-dimensionally divided. Furthermore, the second grooves 210b are provided so as to intersect with the first grooves 210a. The inclination angle of the second grooves 210b is set at, for example, less than 90° such that these may be provided so as to intersect the second grooves 210b and the first grooves 210a.

Moreover, the pitch providing the second grooves 210b is a pitch in which at least one or more through holes are formed in each non-conductive acoustic matching layer 210 as the conductive path. As concrete examples, the groove pitch examples 1 to 4, etc. are mentioned above. Moreover, the through hole is formed in the front-back direction of the ultrasonic transducer (refer to the z direction of FIG. 1).

The cut-in width of the second grooves 210b is determined based on the radiation performance of the ultrasonic pulse, the vibration mode of the ultrasonic transducer, and the formation process of the conductive film. Moreover, the cut-in width is the width of the second grooves 210b, wherein, for example, it may be set at approximately 30% or less of the element width and 10 μm or more. Moreover, regarding the order of establishing the first grooves 210a and the second grooves 210b, either may come first.

Moreover, the processes of forming the conductive film and filling with resin, connecting the block, connecting the piezoelectrics, forming the split grooves, connecting the front substrate and the rear substrate, connecting the backing material, and connecting the acoustic lens of Embodiment 2 are the same as Embodiment 1, so explanations are omitted.

(Function/Effect)

The function and effect of the ultrasonic transducer and the ultrasonic probe related to Embodiment 2 are described.

As described above, in the ultrasonic transducer of Embodiment 2, in each non-conductive acoustic matching layer 210, the first grooves 210a are provided reaching from the boundary surface (back surface of the non-conductive acoustic matching layer 210), with the front surface electrode leading up to the mid-way point. Furthermore, the non-conductive acoustic matching layer 210 is provided with the second grooves 210b leading from the boundary surface with the conductive acoustic matching layer 211 (front surface of the non-conductive acoustic matching layer 210) to the mid-way point of the non-conductive acoustic matching layer 210. The mid-way point is, as mentioned above, the location further backwards than the front edge of the first grooves 210a. Moreover, the crossing part 220 is formed by the first grooves 210a and second grooves 210b. As a result, the through hole leading from the boundary surface with the front surface electrode to the boundary surface with the conductive acoustic matching layer is formed. Furthermore, the conductive film 210c is provided passing from at least the edge of the back surface side to the edge of the front surface side (area leading up to the conductive acoustic matching layer) on the inner surfaces of the first grooves 210a and the second grooves 210b. In other words, the conductive film is provided passing the rear edge of first grooves 210a to the front edge of the second grooves 210b.

Accordingly, by means of providing the first grooves 210a and the second grooves 210b in the non-conductive material block 2101, the conductive path may be formed on the non-conductive acoustic matching layer 210 by the process of forming the through hole and the process of providing the conductive path on the through hole alone. Furthermore, the non-conductive material block 2101, conductive material block, and piezoelectrics material block are layered in order to form the layered body. Next, by means of providing the split cells in the xy direction with respect to the layered body, the two-dimensional array of the element is formed, configured by comprising the piezoelectrics, non-conductive acoustic matching layer 210, and the layered body of the conductive acoustic matching layer.

According to the ultrasonic transducer manufactured by such a manufacturing process, forming the conductive path of the non-conductive acoustic matching layer 210 may be made easier. Consequently, both avoiding the complication of the manufacturing process of the ultrasonic transducer and forming the conductive path from the front surface electrode to the front substrate may be achieved. That is, the manufacturing process is simple if the configuration comprises the first grooves 210a, the second grooves 210b, and the conductive film in the non-conductive acoustic matching layer 210, and furthermore, the conductive path may be provided without fail from the front surface electrode to the conductive acoustic matching layer.

[Embodiment 3]

Figure 18:
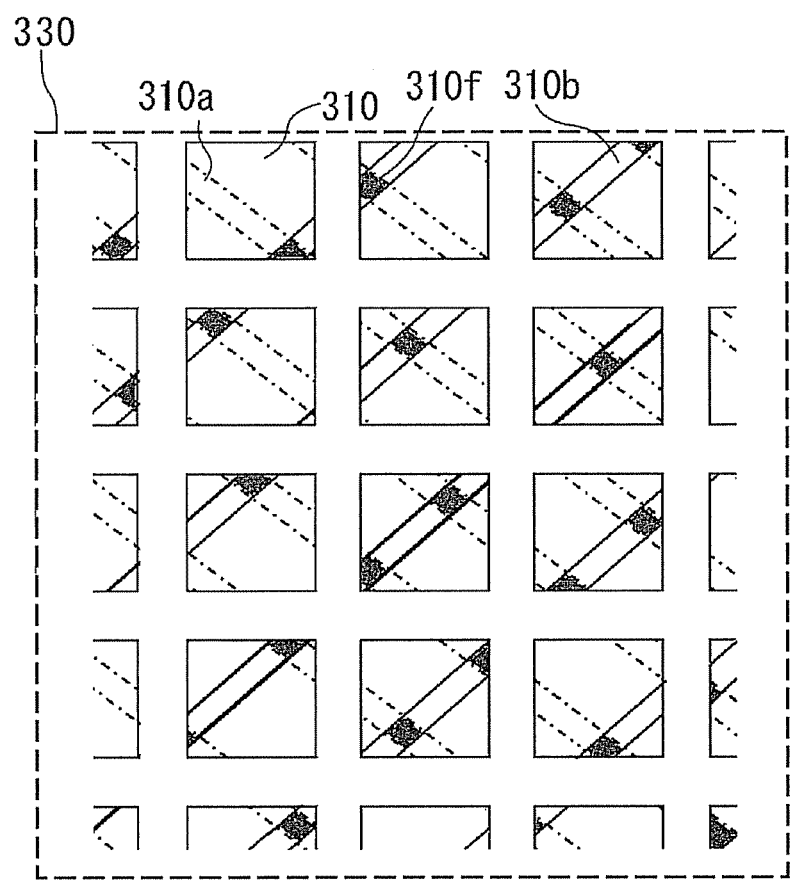
[FIG. 18] is a top schematic perspective view of the non-conductive acoustic matching layer showing the outline of an example of the first grooves and the second grooves provided on the non-conductive acoustic matching layer related to Embodiment 3.

Next, the ultrasonic transducer related to Embodiment 3 and the ultrasonic probe provided with the ultrasonic transducer are described with reference to FIG. 18. FIG. 18 is the top schematic perspective view of the non-conductive acoustic matching layer of Embodiment 3, and shows the abstract of an example of the first grooves and the second grooves provided in the non-conductive acoustic matching layer of the ultrasonic transducer. The non-conductive acoustic matching layer group 330 indicated by dashed lines in the figure shows the entire two-dimensional array element sequence of the non-conductive acoustic matching layer 310 as one conceptual bundle with dashed lines. Moreover, regarding Embodiment 3, only parts differing from Embodiment 2 are described and descriptions of other overlapping areas are omitted. Moreover, the number of first grooves 310a and second grooves 310b shown in FIG. 18 is conceptually shown.

As shown in FIG. 18, in the ultrasonic transducer of Embodiment 3, both the first grooves 310a and the second grooves 310b provided in the non-conductive acoustic matching layer 310 are inclined. Moreover, the grooves indicated by solid lines in FIG. 18 are the second grooves 310b, and the grooves indicated by dashed lines are the first grooves 310a.

That is, the second grooves 310b in Embodiment 3 are provided inclining towards the element array direction, and the first grooves 310a are also provided inclining towards the element array direction. Moreover, in the same manner as Embodiment 2, the second grooves 310b and the first grooves 310a intersect at the mid-way point of the front-back direction (refer to the z direction of FIG. 1) of the non-conductive acoustic matching layer 310. Moreover, as shown in FIG. 18, at least one or more of the crossing part 310f at which the second grooves 310b and the first grooves 310a intersect is provided in each non-conductive acoustic matching layer 310.

Moreover, the groove pitch of the second grooves 310b and the first grooves 310a in Embodiment 3 may be set according to the groove pitch examples 1 to 4 described in Embodiment 2.

(Function/Effect)

The function and effect of the ultrasonic transducer and the ultrasonic probe related to Embodiment 3 are described.

In the ultrasonic transducer of Embodiment 3, the first grooves 310a are provided for each non-conductive acoustic matching layer reaching from the boundary surface (back surface of the non-conductive acoustic matching layer 310), with the front surface electrode leading up to the mid-way point. Furthermore, the second grooves 310b are provided leading from the boundary surface with the conductive acoustic matching layer (front surface of the non-conductive acoustic matching layer 310) to the mid-way point of the non-conductive acoustic matching layer 310. The mid-way point is the location further backwards than the front edge of the first grooves 310a. Moreover, the crossing part 310f is formed by the first grooves 310a and second grooves 310b. As a result, the through hole leading from the boundary surface with the front surface electrode to the boundary surface with the conductive acoustic matching layer is formed. Furthermore, the conductive film 310c is provided passing from at least the edge of the back surface side to the edge of the front surface side (area leading up to the conductive acoustic matching layer) inside the first grooves 310a and the second grooves 310b. In other words, the conductive film is provided passing the rear edge of first grooves 310a to the front edge of the second grooves 310b.

Accordingly, by means of providing the first grooves 310a and the second grooves 310b, the conductive path may be formed on the non-conductive acoustic matching layer 310 by the process of forming the through hole and the process of providing the conductive path on the through hole alone. Furthermore, the non-conductive material block, conductive material block, and piezoelectrics material block are layered in order to form the layered body. Next, by means of providing the split cells in the xy direction with respect to the layered body, the two-dimensional array of the element is formed, configured by comprising the piezoelectrics, non-conductive acoustic matching layer 310, and the layered body of the conductive acoustic matching layer.

According to the ultrasonic transducer manufactured by the manufacturing process, forming the conductive path of the non-conductive acoustic matching layer 310 may be made easier. Consequently, both may be achieved that complications in the manufacturing process of the ultrasonic transducer are avoided and the conductive path from the front surface electrode to the front substrate is formed. That is, it is a configuration in which the first grooves 310a, the second grooves 310b, and the conductive film are present in the non-conductive acoustic matching layer 310, the manufacturing process thereof is simple, and furthermore, the conductive path may be provided without fail from the front surface electrode to the conductive acoustic matching layer.

[Modified Example]

Next, modified examples of the ultrasonic transducer of Embodiments 1 to 3 mentioned above are described. Regarding the configuration of the ultrasonic transducer mentioned above, the conductive acoustic matching layers (111, etc.) are arranged on the front surface side of the non-conductive acoustic matching layers (110, etc.), and the front substrates (122, etc.) are arranged on the front surface side of the conductive acoustic matching layer. Moreover, the non-conductive acoustic matching layer and the front substrate are electrically connected via the conductive acoustic matching layer. However, the ultrasonic transducers of the embodiments are not limited to the configurations. For example, it may be a configuration in which the front substrate is provided on the front surface side of the non-conductive acoustic matching layer without comprising the conductive acoustic matching layer.

In the ultrasonic transducer of Embodiment 1 to Embodiment 3 in which the modified embodiment was applied, both avoiding complications in forming the conductive path of the non-conductive acoustic matching layer and forming the conductive path from the front surface electrode to the front substrate may be achieved.

The embodiments of the present invention were described; however, the embodiments described above were presented as examples and are not intended to limit the range of the invention. The new embodiments may be carried out in various other configurations, and various abbreviations, replacements, and changes may be made in a range not departing from the summary of the invention. These embodiments and deformations thereof are included in the range and summary of the invention and included in the invention described in the range of patent claims as well as the range of the equivalent thereof.

EXPLANATION OF SYMBOLS

100 Ultrasonic transducer
110, 210, 310 Non-conductive acoustic matching layer
110a, 210a, 310a First grooves
110b, 210b, 310b Second grooves
110c, 210c Conductive film
110d Resin
110e Through hole
110f, 310f Crossing part
111, 211 Conductive acoustic matching layer
112 Front surface electrode
114 Piezoelectrics
116 Back surface electrode
118 Backing material
120 Rear substrate
122 Front substrate
230 Non-conductive acoustic matching layer groups
1101, 2101 Non-conductive material block
1111 Conductive material block
1141 Piezoelectrics material block
Pe Element pitch
Pk Groove pitch
Pw Element width

What is claimed is:

1. An ultrasonic transducer, comprising:
a plurality of piezoelectrics which are two-dimensionally arranged,
electrodes provided on each of the plurality of piezoelectrics,
non-conductive acoustic matching layers with a first surface on the electrode side and a second surface on the opposite side of the first surface, and which are two-dimensionally arranged according to the piezoelectrics, and
substrates arranged on the second surface side,
first grooves provided on each of the first surfaces, the first grooves having depth leading up to the mid-way point between the first surface and the second surface,
second grooves provided on each of the second surfaces, the second grooves having depth leading up to at least the mid-way point and intersecting the first grooves, wherein,
the electrode and the second surface are conducted via the first grooves, the intersections of the first grooves and the second grooves, and the second grooves.

2. The ultrasonic transducer according to claim 1, further comprising conductive acoustic matching layer which is a two-dimensionally arranged between the non-conductive acoustic matching layer and the substrate according to the piezoelectrics.

3. The ultrasonic transducer according to claim 1, wherein, at least one the intersections is formed in response to each of the plurality of piezoelectrics.

4. The ultrasonic transducer according to claim 3, wherein, the first grooves are provided with the first pitch which is substantially equal to the pitch of the plurality of piezoelectrics.

5. The ultrasonic transducer according to claim 3, wherein, the first grooves are provided with the first pitch which has the width of the piezoelectrics or less, and
the following formula is satisfied:

$$Pk_1/\sin\theta \leq Pw$$

where Pw is the width of the piezoelectrics, $Pk_1$ is the first pitch, and $\theta$ is the angle of the array direction of the piezoelectrics and the first grooves.

6. The ultrasonic transducer according to claim 5, wherein, the $\theta$ is more than 0° and less than 90°.

7. The ultrasonic transducer according to claim 3, wherein, the second grooves are provided with the second pitch which is equal to or less than width of the piezoelectrics, and
the following formula is satisfied:

$$Pk_2/\sin\theta \leq Pw \text{ and}$$

where Pw is the width of the piezoelectrics, $Pk_2$ is the second pitch, and $\theta$ is angle of the array direction of the piezoelectrics and the second grooves.

8. The ultrasonic transducer according to claim 7, wherein, the $\theta$ is more than 0° and less than 90°.

9. The ultrasonic transducer according to claim 3, wherein, the following formula is satisfied:

$$Pk_3/\sin\theta = Pe$$

where Pe is the pitch of the non-conductive acoustic matching layer, $Pk_3$ is the pitch of the first grooves, and $\theta$ is the angle of the array direction of the piezoelectrics and the first grooves.

10. The ultrasonic transducer according to claim 9, wherein, the θ is more than 0° and less than 90°.

11. The ultrasonic transducer according to claim 3, wherein, the second grooves are provided with the second pitch which is substantially equal to the pitch of the plurality of piezoelectrics.

12. The ultrasonic transducer according to claim 1, wherein, the following formula is satisfied:

$$Pk_4/\sin\theta = Pe$$

where Pe is the pitch of the non-conductive acoustic matching layer, $Pk_4$ is the pitch of the second grooves, and θ is the angle of the array direction of the piezoelectrics and the second grooves.

13. The ultrasonic transducer according to claim 12, wherein, the θ is more than 0° and less than 90°.

14. The ultrasonic transducer according to claim 1, wherein, a conductive material is provided on the inner surfaces of the first grooves.

15. The ultrasonic transducer according to claim 1, wherein, the conductive material is provided on the inner surfaces of the second grooves.

16. The ultrasonic transducer according to claim 1, wherein, the plurality of piezoelectrics are two-dimensionally arranged along a first direction and a second direction perpendicular to each other, the first grooves are arranged along the first direction, the second grooves are arranged along the second direction, the first grooves are provided such that they penetrate the non-conductive acoustic matching layers corresponding to the first direction, and the second grooves are provided such that they penetrate the non-conductive acoustic matching layers corresponding to the second direction.

17. An ultrasonic probe, comprising:

an ultrasonic transducer, and an interface between the ultrasonic transducer and an external device, wherein, the ultrasonic transducer comprises:

a plurality of piezoelectrics which are two-dimensionally arranged, electrodes provided on each of the plurality of piezoelectrics, a non-conductive acoustic matching layers comprising the first surface of the electrode side and the second surface, which are the opposite side of the first surface, and substrates arranged on the second surface side, wherein, first grooves provided on each of the first surfaces, the first grooves having depth leading up to the mid-way point between the first surface and the second surface, second grooves provided on each of the second surface, the second grooves having depth leading up to at least the mid-way point, and intersecting the first groove, and the electrode and the second surface are conducted via the first grooves, the intersections of the first grooves and the second grooves, and the second grooves.

* * * * *